(12) United States Patent
Xu et al.

(10) Patent No.: US 9,563,016 B1
(45) Date of Patent: Feb. 7, 2017

(54) SUBWAVELENGTH PHOTONIC CRYSTAL WAVEGUIDE WITH TRAPEZOIDAL SHAPED DIELECTRIC PILLARS IN OPTICAL SYSTEMS

(71) Applicants: Xiaochuan Xu, Austin, TX (US); Ray T. Chen, Austin, TX (US)

(72) Inventors: Xiaochuan Xu, Austin, TX (US); Ray T. Chen, Austin, TX (US)

(73) Assignee: Omega Optics, Inc., Austin, TX (US)

( * ) Notice: Subject to any disclaimer, the term of this patent is extended or adjusted under 35 U.S.C. 154(b) by 0 days.

(21) Appl. No.: 14/951,464

(22) Filed: Nov. 24, 2015

(51) Int. Cl.
| | |
|---|---|
| *G02F 1/01* | (2006.01) |
| *G02B 6/125* | (2006.01) |
| *G02B 6/122* | (2006.01) |
| *G02B 6/10* | (2006.01) |
| *G02B 6/293* | (2006.01) |
| *G02F 1/365* | (2006.01) |
| *G02B 6/34* | (2006.01) |

(52) U.S. Cl.
CPC ............. *G02B 6/125* (2013.01); *G02B 6/107* (2013.01); *G02B 6/1225* (2013.01); *G02B 6/1228* (2013.01); *G02B 6/29338* (2013.01); *G02B 6/29395* (2013.01); *G02B 6/34* (2013.01); *G02F 1/0147* (2013.01); *G02F 1/365* (2013.01)

(58) Field of Classification Search
CPC ........ G02B 6/125; G02B 6/107; G02B 6/1225; G02B 6/1228; G02F 1/0147; G02F 1/365; G01N 21/253
See application file for complete search history.

(56) References Cited

U.S. PATENT DOCUMENTS

2010/0135616 A1*  6/2010  Watte ................. G02B 6/02366
                                                                    385/50
2014/0325827 A1*  11/2014  Lipson .................. G02B 6/125
                                                                    29/592

* cited by examiner

*Primary Examiner* — Uyen Chau N Le
*Assistant Examiner* — Hoang Tran
(74) *Attorney, Agent, or Firm* — Taboada Law Firm, PLLC; John M. Taboada

(57) ABSTRACT

A method for reducing loss in a subwavelength photonic crystal waveguide bend is disclosed. The method comprising: forming the subwavelength photonic crystal waveguide bend with a series of trapezoidal shaped dielectric pillars centered about a bend radius; wherein each of the trapezoidal shaped dielectric pillars comprise a top width, a bottom width, and a trapezoid height; wherein the length of the bottom width is greater than the length of the top width; and wherein the bottom width is closer to the center of the bend radius of the subwavelength photonic crystal waveguide bend than the top width. Other embodiments are described and claimed.

17 Claims, 28 Drawing Sheets

Figure 1A:
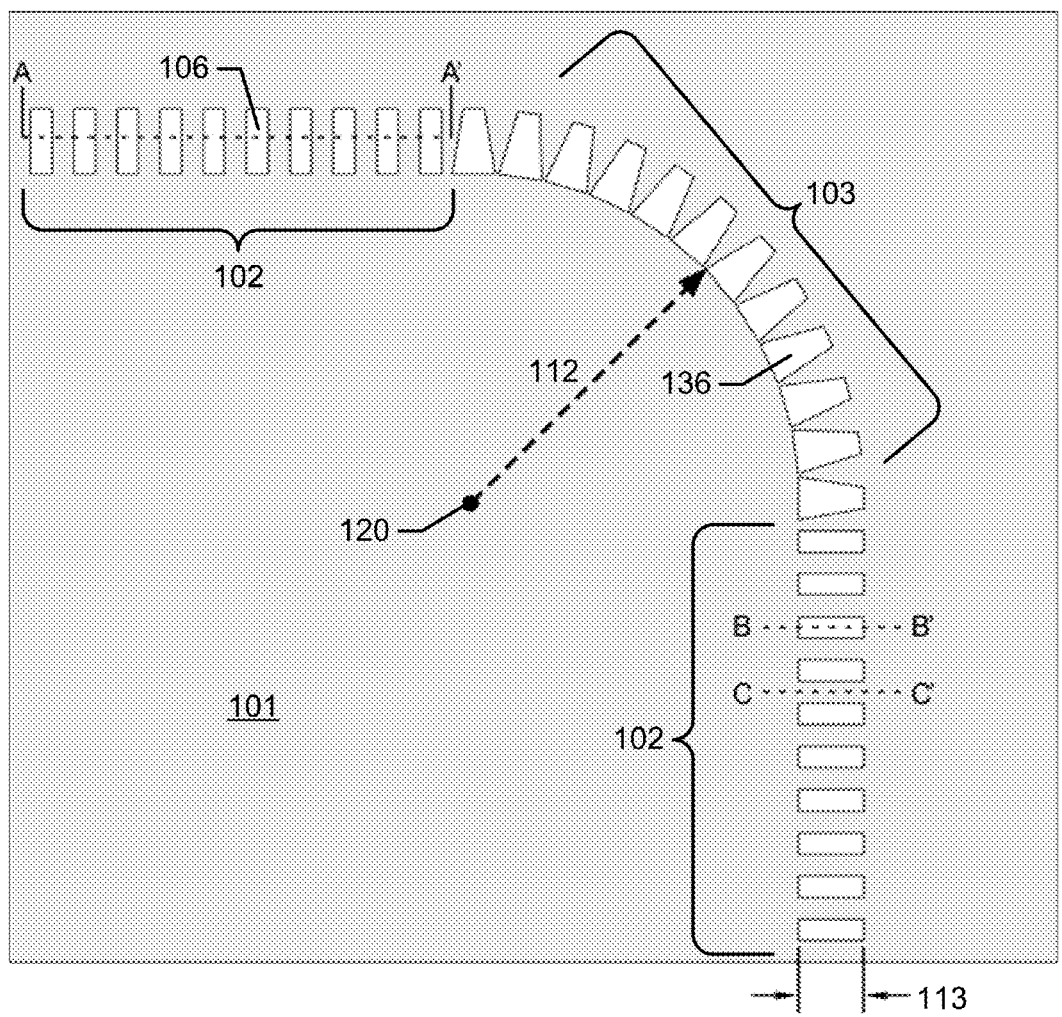

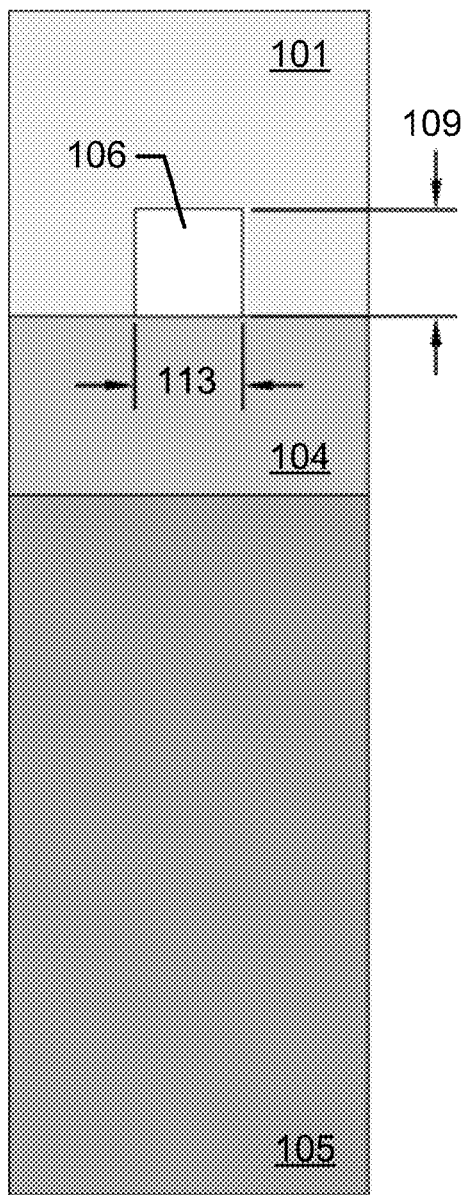
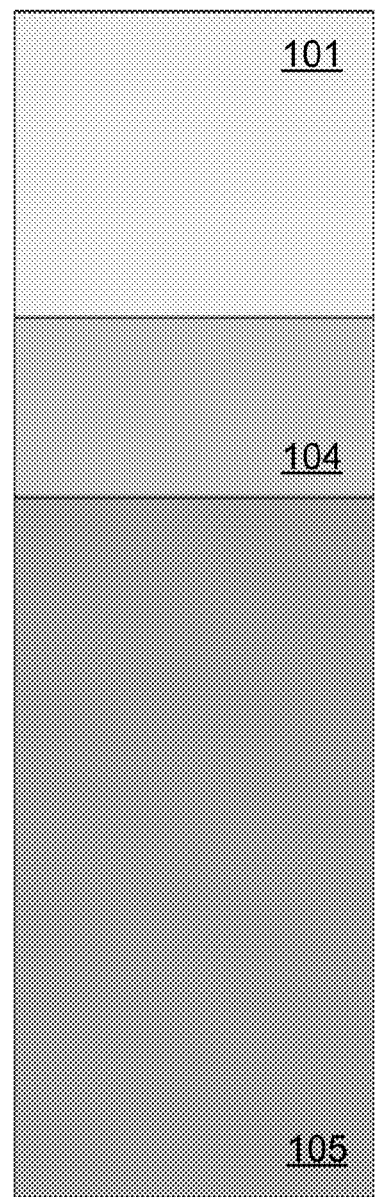
*Fig. 1C*        *Fig. 1D*

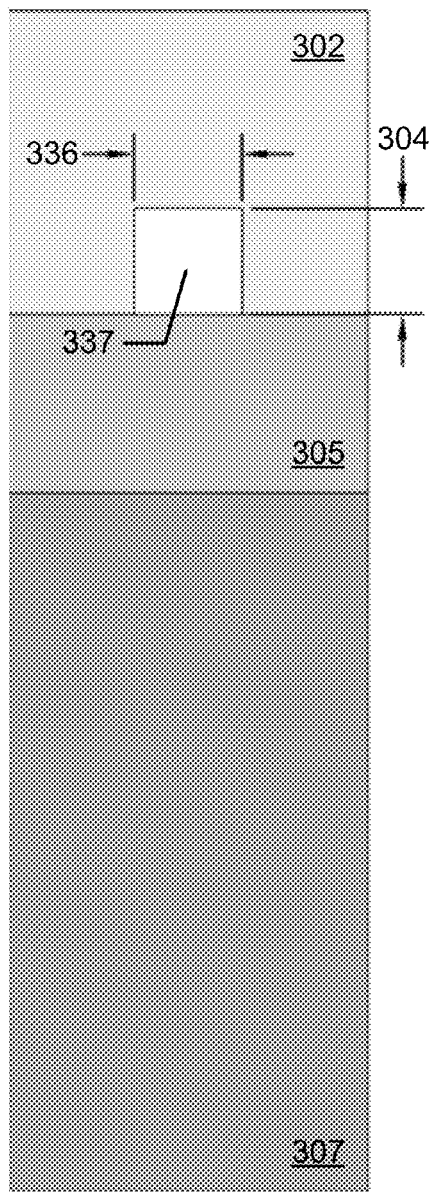 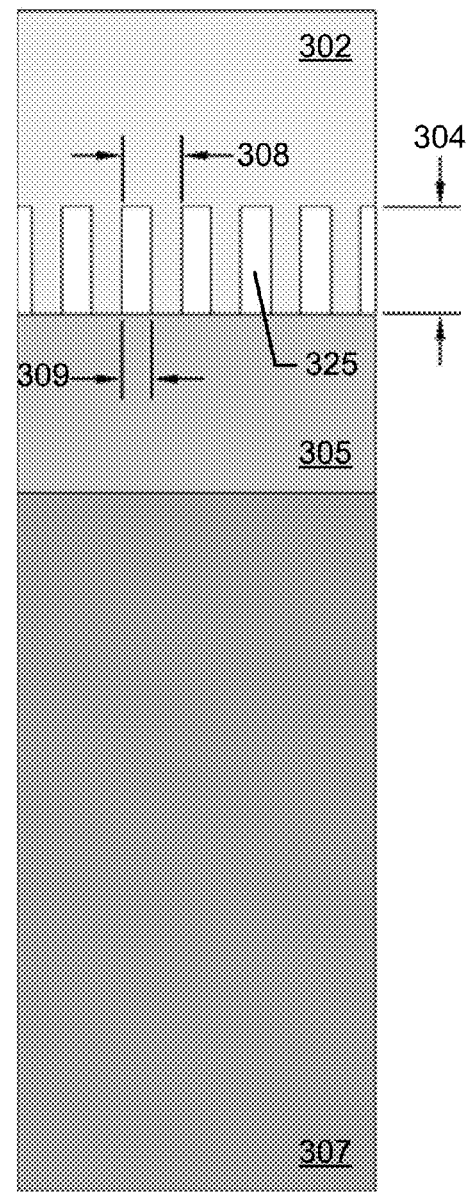
*Fig. 3D*  *Fig. 3E*

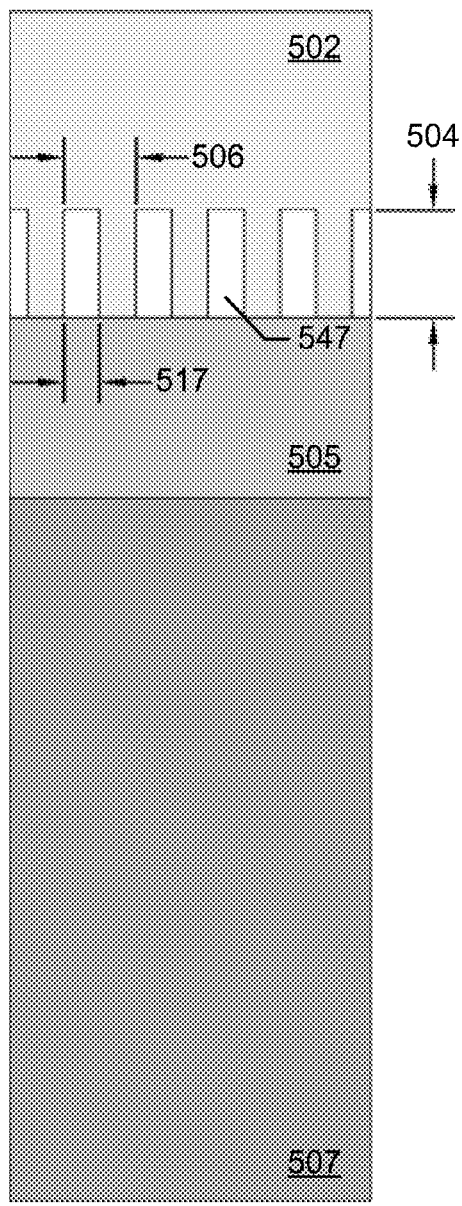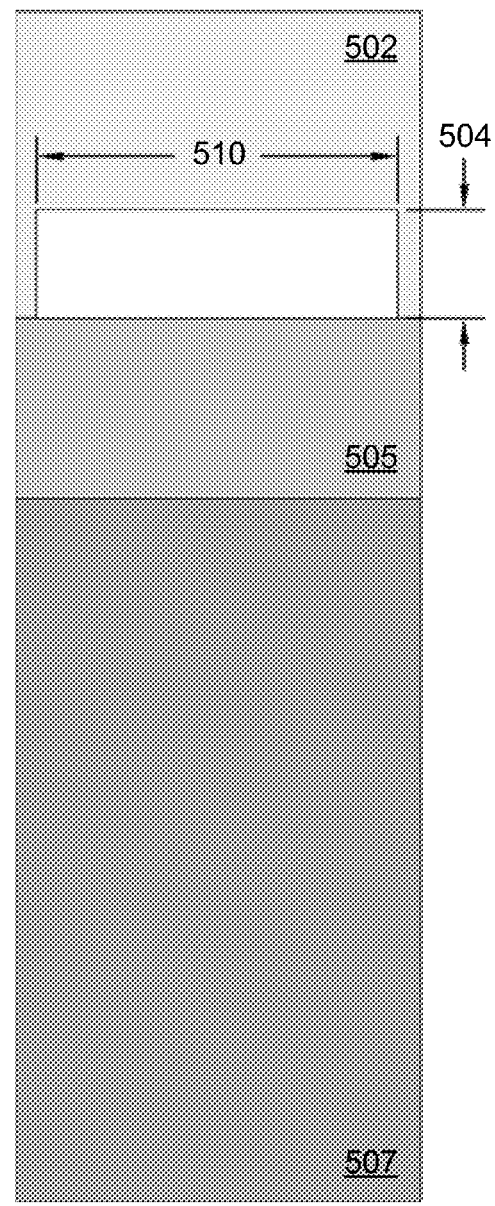
*Fig. 5B*  *Fig. 5C*

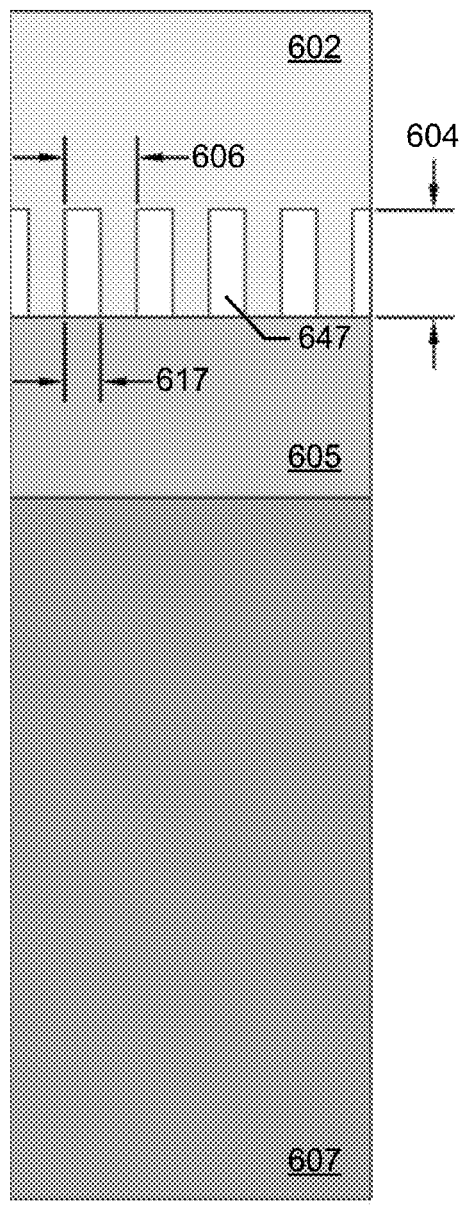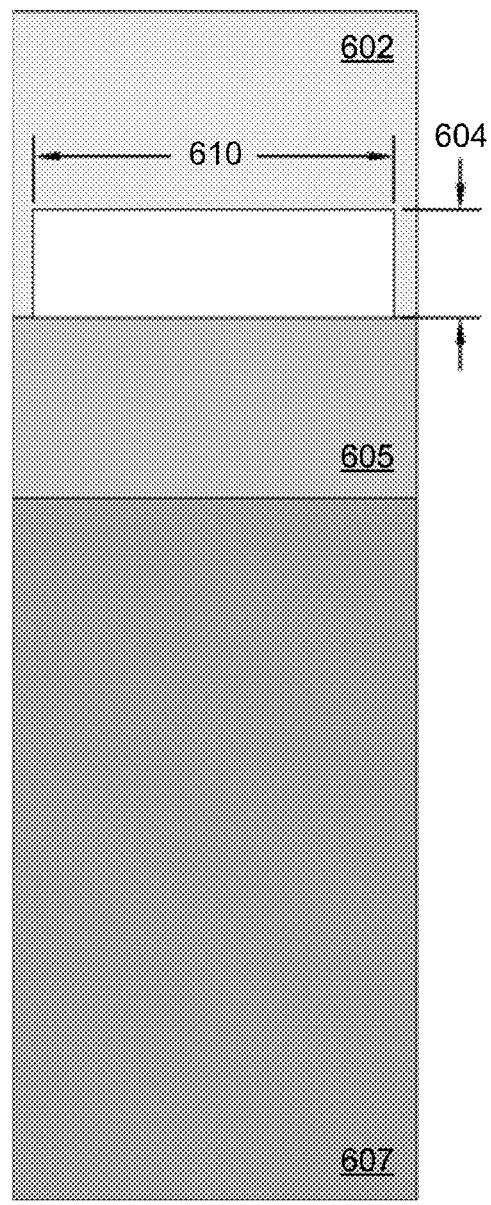
*Fig. 6B*          *Fig. 6C*

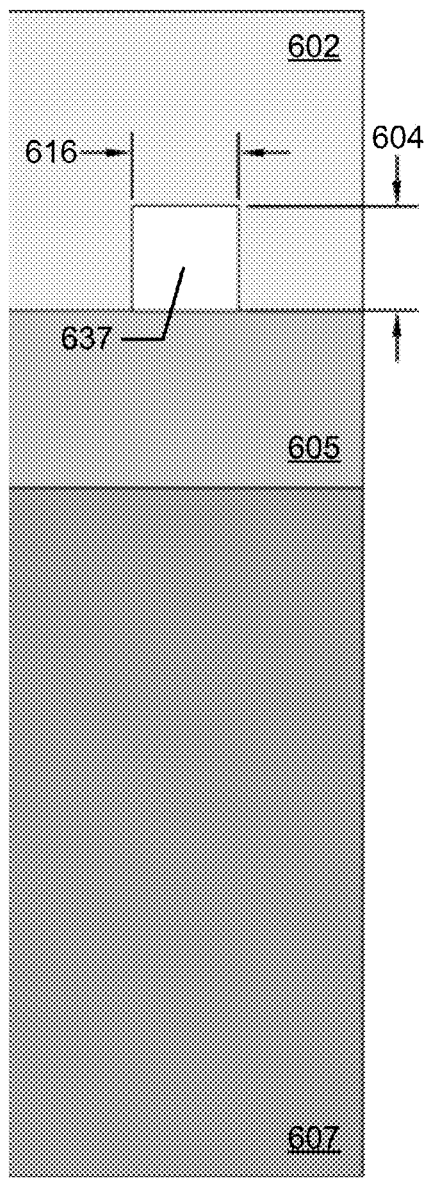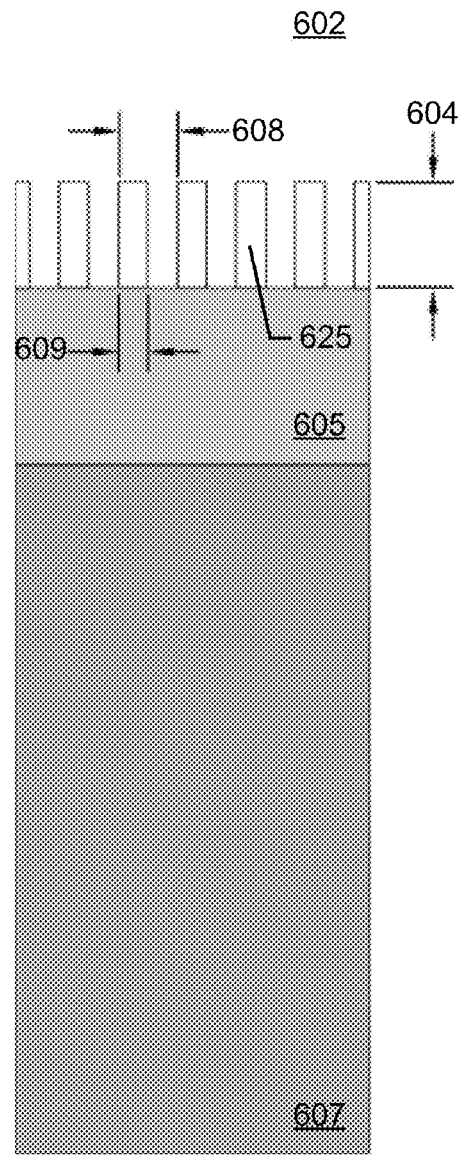
*Fig. 6D*          *Fig. 6E*

SUBWAVELENGTH PHOTONIC CRYSTAL WAVEGUIDE WITH TRAPEZOIDAL SHAPED DIELECTRIC PILLARS IN OPTICAL SYSTEMS

I. STATEMENT REGARDING FEDERALLY SPONSORED RESEARCH

This invention was made with Government support under grant DE-SC0013178 awarded by the Department of Energy (DOE). The Government has certain rights in this invention.

II. BACKGROUND

Field of the Invention

The present disclosure relates generally to the field of optical and medical devices, and more specifically to an apparatus and method for optical communication, biological sensing, and chemical sensing.

Background of the Invention

The statements in this section merely provide background information related to the present disclosure and may not constitute prior art.

Silicon photonics has been attracting intense interest in the last decade due to its great potential in realizing low cost photonic chips with the readily-available CMOS manufacture technology. However, the fact that silicon does not have either a direct band gap or a second-order nonlinearity makes it a great challenge to generate or control photons. Additionally, the large refractive index contrast weakens the photon-matter interaction and makes silicon a less attractive sensing platform. The lack of direct band gap or second-order nonlinearity may potentially be solved by hybrid integration of silicon and functional cladding material and this issue along with the issue of the large refractive index may be solved by a waveguiding structure that facilitates the photon-matter interactions.

Plenty of structures, such as slot waveguides and photonic crystal waveguides have been exploited to enhance the photon-matter interaction. Subwavelength photonic crystal waveguides, comprised of periodically arranged high index and low index materials with a pitch of less than one wavelength, have received considerable attention in recent years. Bloch modes may be supported by this periodic arrangement of silicon pillars and cladding material, and therefore photons may propagate in theory without being attenuated by the discontinuity of the mediums. Subwavelength photonic crystal waveguides provide another dimension of freedom to precisely control a few important waveguide properties such as refractive index, dispersion, and mode overlap volume, which are determined by the materials comprising the waveguides as demonstrated previously. The control of these properties enables significant improvements over conventional waveguide based devices such as grating couplers, directional couplers, sensors, filters, and modulators.

One critical problem remaining unresolved is the large loss of the subwavelength photonic crystal waveguide bends. For instance, a 10 μm radius 90° bend has an insertion loss of ~1.5 dB. To avoid the substantial loss introduced by a subwavelength photonic crystal waveguide bend, the subwavelength photonic crystal waveguide is tapered to conventional strip waveguides before reaching a bend and further tapered back to subwavelength photonic crystal waveguides afterwards. Although the strip waveguide bends can significantly reduce the loss, the taper adds additional loss and wastes the precious silicon chip surface. Therefore, to achieve the goal of building integrated photonic systems with entirely subwavelength photonic crystal waveguides, a low loss and small bend radius subwavelength photonic crystal waveguide bend is highly desirable. In addition, the low loss bend is an essential component for high quality factor subwavelength photonic crystal waveguide ring resonators, which can be used for optical modulators, switches, filters, and sensors.

III. SUMMARY

A trapezoidal shaped dielectric pillar based subwavelength photonic crystal waveguide bend is proposed herein, that is unique in that it provides the freedom to control the refractive index profile across the cross-section of a waveguide and therefore reduce the bend loss of a subwavelength photonic crystal waveguide. Compared to a straight waveguide, waveguide bends usually have additional loss due to the mode delocalization. The delocalized mode causes the mode mismatch between the straight and bend waveguide and hence excessive radiation loss. The mode delocalization is not prominent when the refractive index contrast between the waveguide core and cladding (e.g. silicon) is large and the bend radius is large. As an example, the insertion loss of a silicon strip waveguide bend can be ignored when its radius is larger than 1 μm. The equivalent refractive index of the subwavelength photonic crystal waveguide is relatively small so that the bending loss cannot be ignored. With the trapezoidal shaped dielectric pillars, the equivalent refractive index along the radial direction can be controlled to shift the mode back to the center of the subwavelength photonic crystal waveguide.

With the trapezoidal shaped subwavelength photonic crystal waveguide bend, the quality factor of the subwavelength ring resonator may be significantly improved. A typical optical system employing the high quality factor ring resonator may comprise: a substrate with a bottom cladding to support the structure, a light source, couplers to interface the light source and the optical circuits, tapers to convert the light from a conventional waveguide into a subwavelength photonic crystal waveguide, a ring resonator formed by a periodic arrangement of trapezoidal shaped dielectric pillars, and a subwavelength photonic crystal bus waveguide.

The system may comprise a second-order nonlinear material or a third-order nonlinear material as the top cladding. The complex amplitude of light passing through the system may be changed when the properties of the nonlinear material is changed by electric field, magnetic field, electromagnetic field, optical field, and/or mechanical pressure. The system may comprise electrodes or antennas to improve the performance, and accordingly the system may be an optical modulator, all-optical switch, electro-magnetic sensor, or mechanical sensor.

The thermo-optical coefficients of the cladding and the core materials of the dielectric pillars may have opposite signs. The system may be temperature-independent when the size of the pillars is optimized so that the equivalent thermo-coefficient of the composite material is zero. This feature can be used in passive devices such as optical filters.

The system may also be used with cladding materials in liquid and gas phase such as air and solvents. The complex amplitude of light passing through the system is changed when the analytes in air and solvents interact with the optical field of the guided mode. The presence and quantities of the analytes may be determined by interpreting the change of the complex amplitude of light. Accordingly, the system may be used as a chemical sensor and biosensor.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure. Other objectives and advantages of the present invention will become apparent from the following descriptions, taken in connection with the accompanying drawings, wherein, by way of illustration and example, an embodiment of the present invention is disclosed.

IV. BRIEF DESCRIPTION OF THE DRAWINGS

The drawings constitute a part of this specification and include exemplary embodiments of the present invention, which may be embodied in various forms. The drawings described herein are for illustrative purposes only of selected embodiments and not of all possible implementations, and are not intended to limit the scope of the present disclosure in any way. It is to be understood that in some instances, various aspects of the present invention may be shown exaggerated or enlarged to facilitate an understanding of the invention.

Figure 1B:
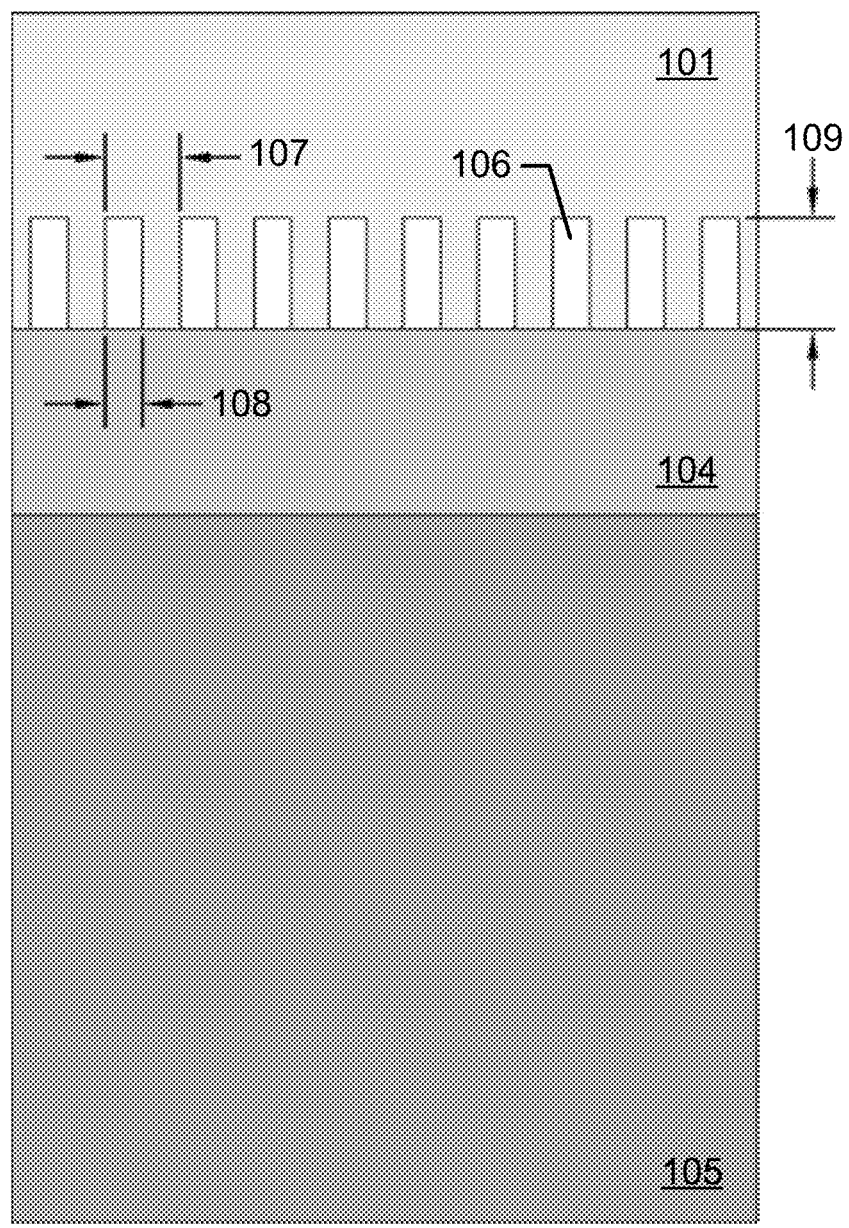
Figure 1E:
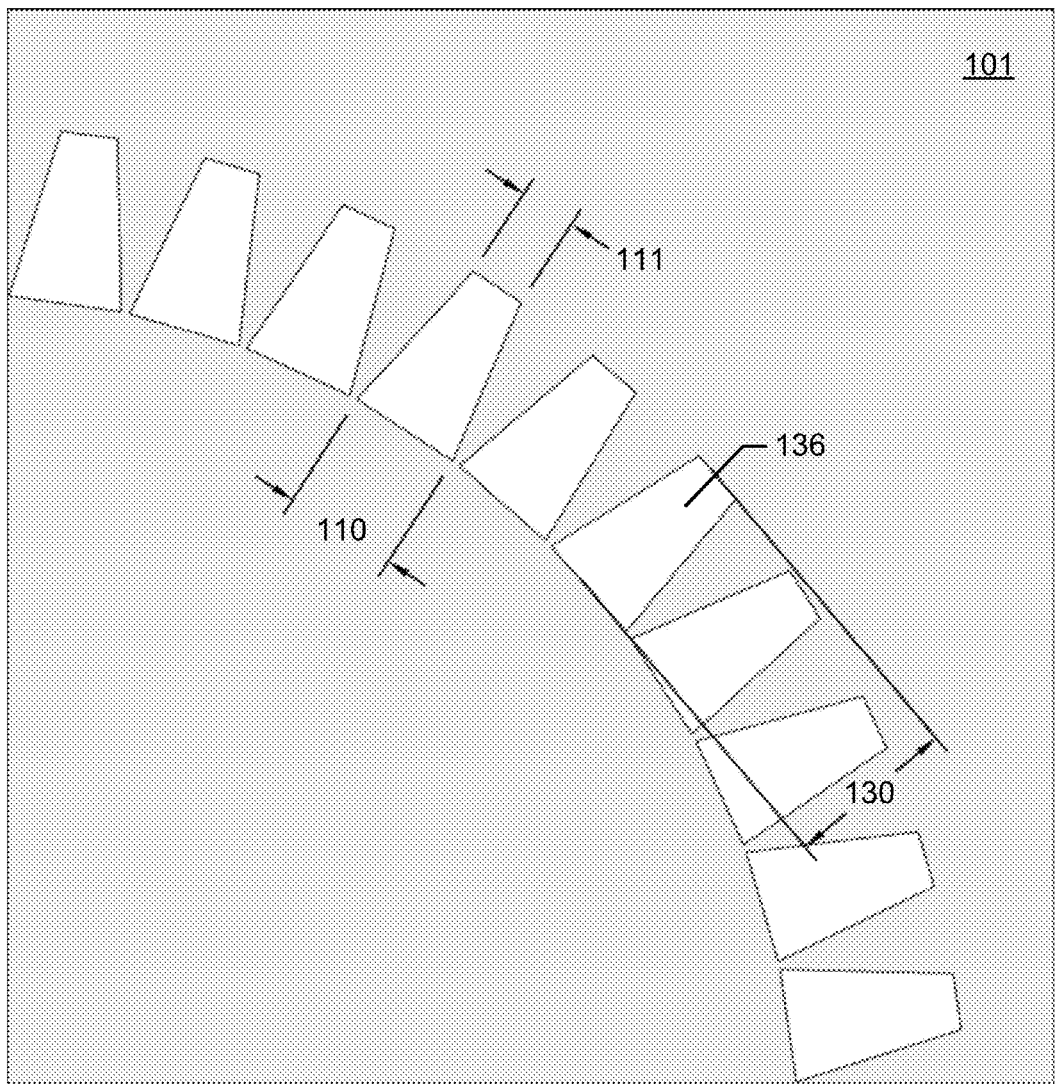

A more complete and thorough understanding of the present invention and benefits thereof may be acquired by referring to the following description together with the accompanying drawings, in which like reference numbers indicate like features, and wherein:

FIG. 1A is a top view schematic drawing of a trapezoidal shaped subwavelength photonic crystal waveguide bend, in accordance with some embodiments. FIG. 1B, FIG. 1C, and FIG. 1D are the cross-sections taken along the dashed lines A-A', B-B', and C-C' of FIG. 1A, respectively. FIG. 1E is a magnified schematic drawing showing a section of the trapezoidal shaped pillar of the waveguide bend in FIG. 1A.

Figure 2A:
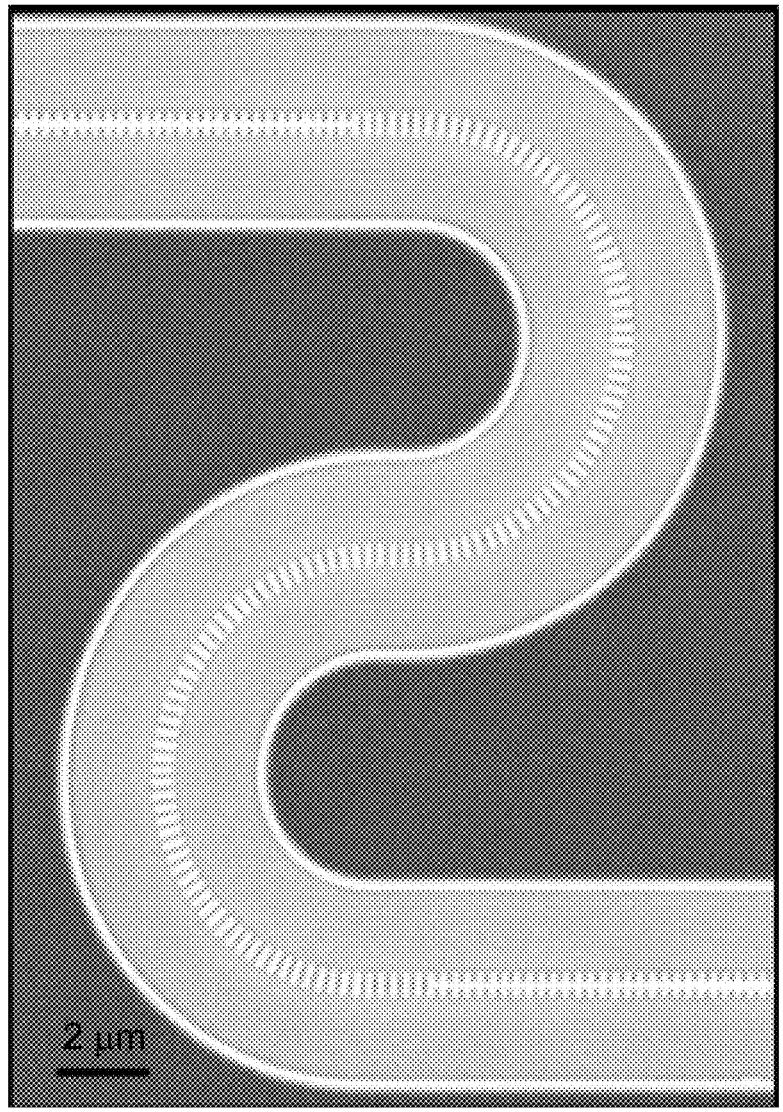
Figure 2B:
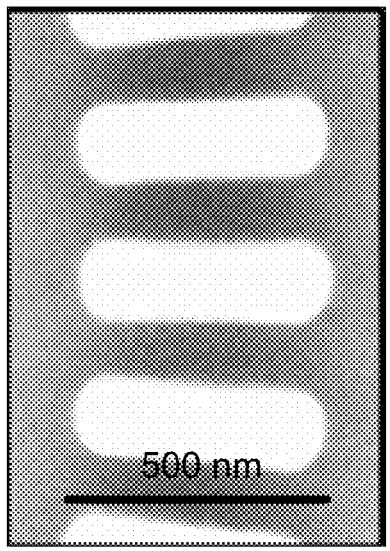
Figure 2C:
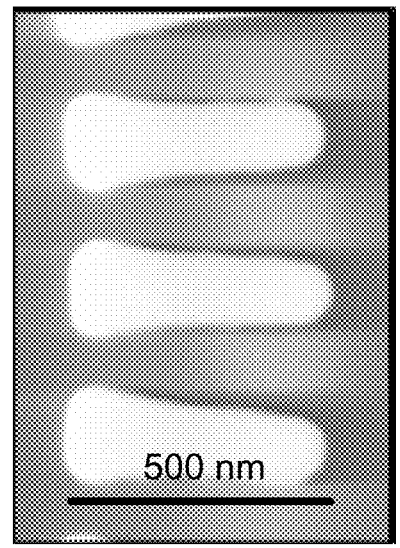
Figure 2D:
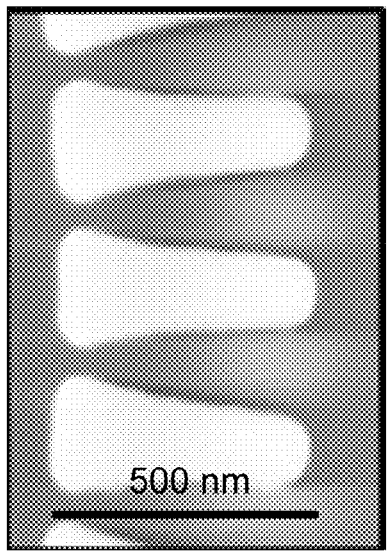
Figure 2E:
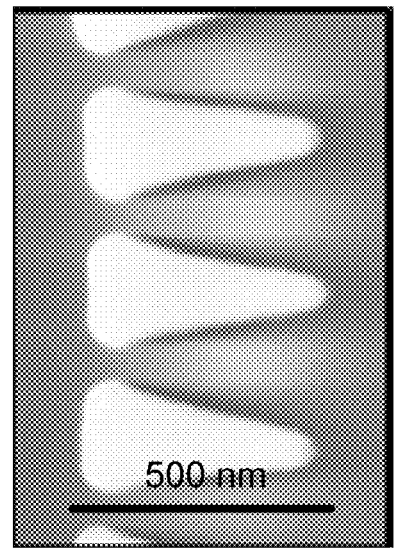
Figure 2F:
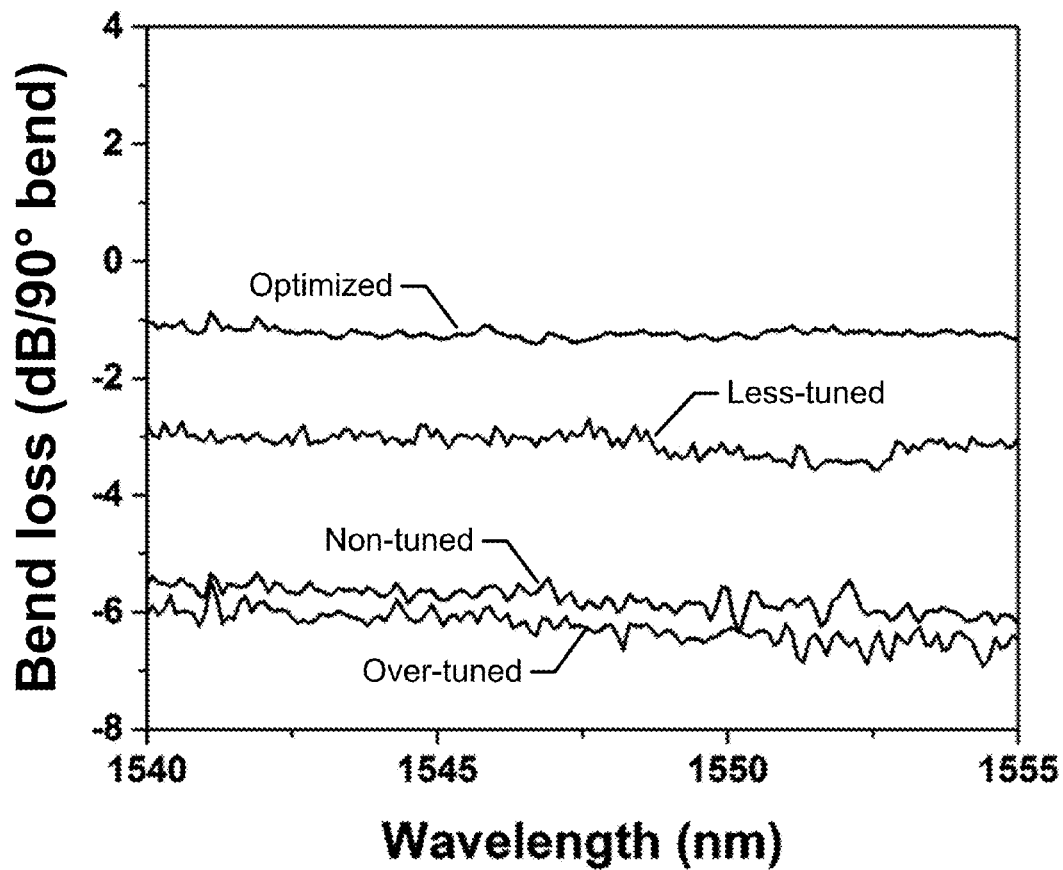
Figure 2G:
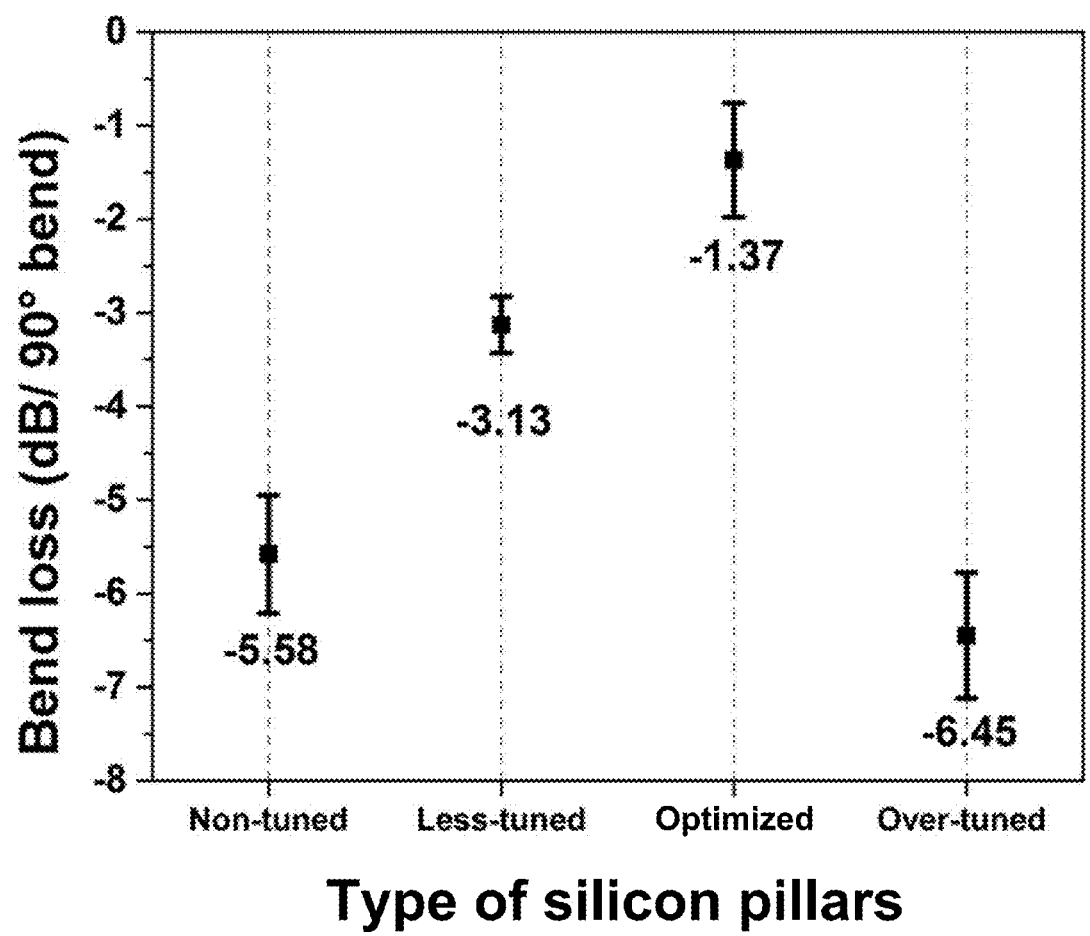

FIG. 2A is a scanning electron microscopy (SEM) image of a subwavelength photonic crystal waveguide bend comprising four 90° bends, in accordance with some embodiments. FIG. 2B is an SEM image of a conventional rectangular waveguide bend, while FIGS. 2C-2E are the trapezoidal shaped waveguide bends with different top and base width. FIG. 2F shows the transmission spectra of the subwavelength photonic crystal waveguide bends. FIG. 2G is the bend loss of the four different bends, showing that trapezoidal shaped waveguide bends may reduce the bend loss from −6.45 dB to −1.37 dB.

Figure 3A:
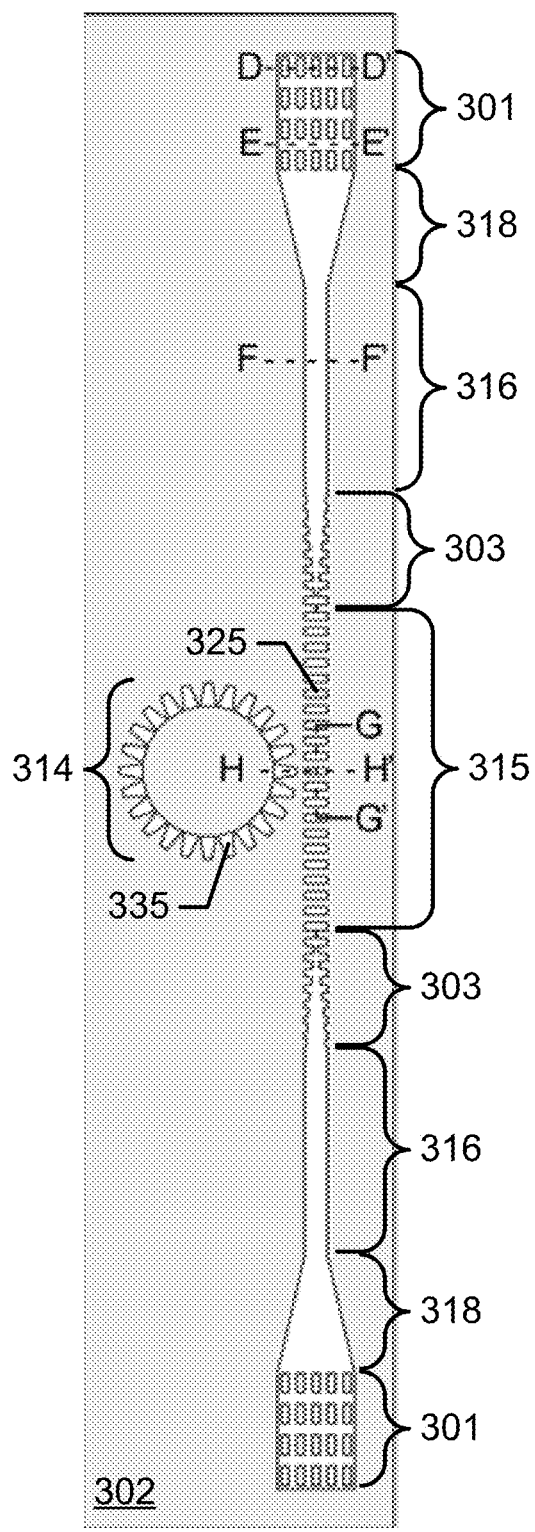
Figure 3B:
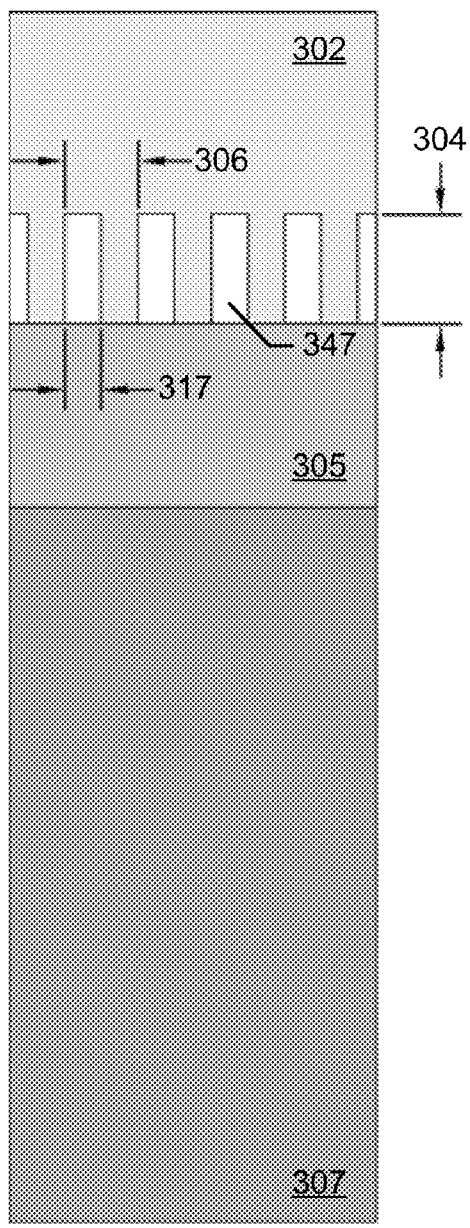
Figure 3C:
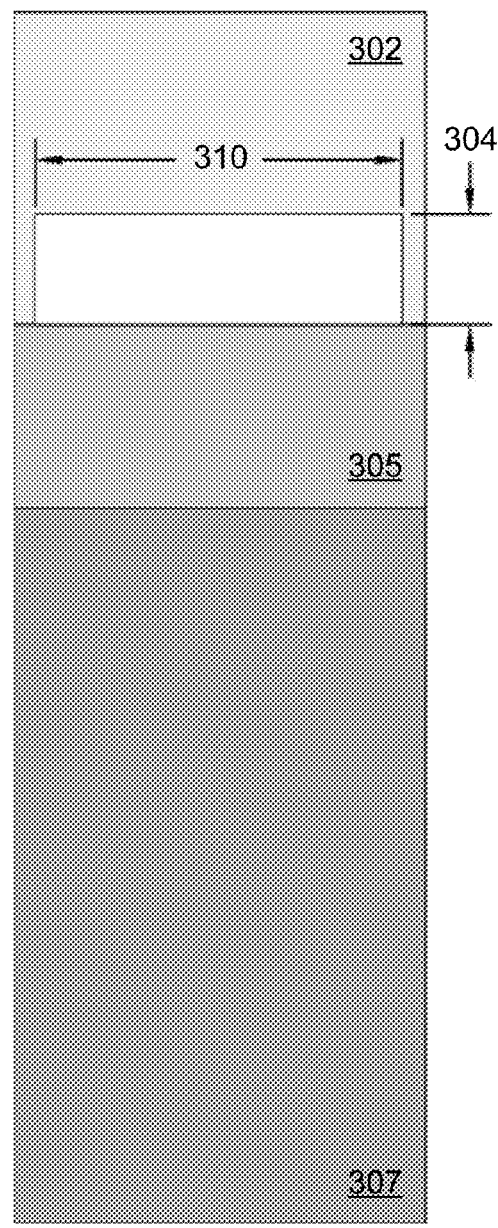
Figure 3F:
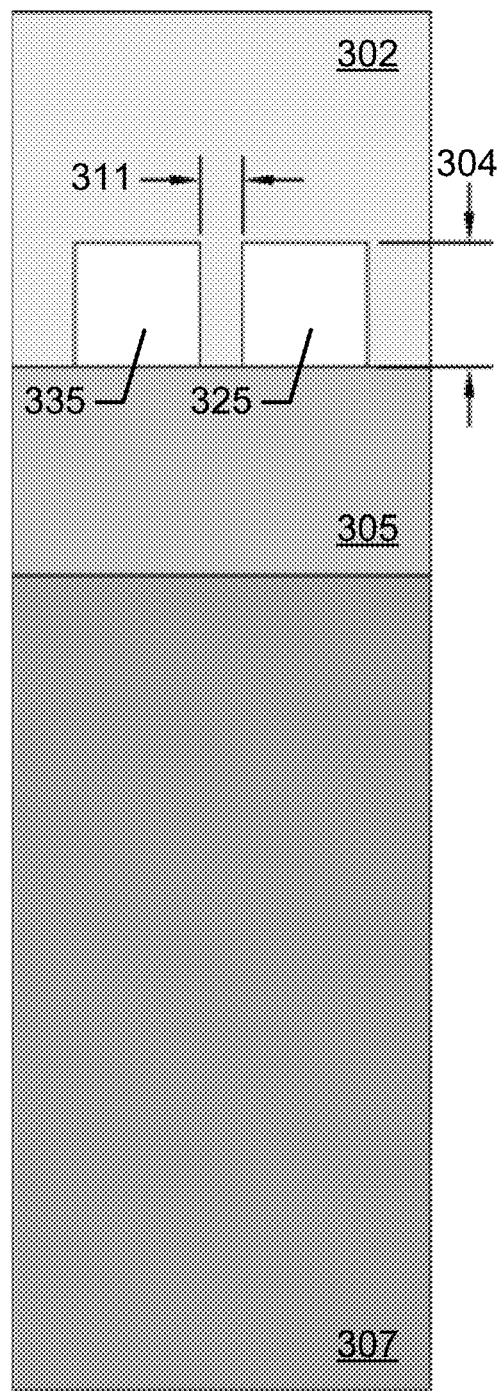
Figure 3G:
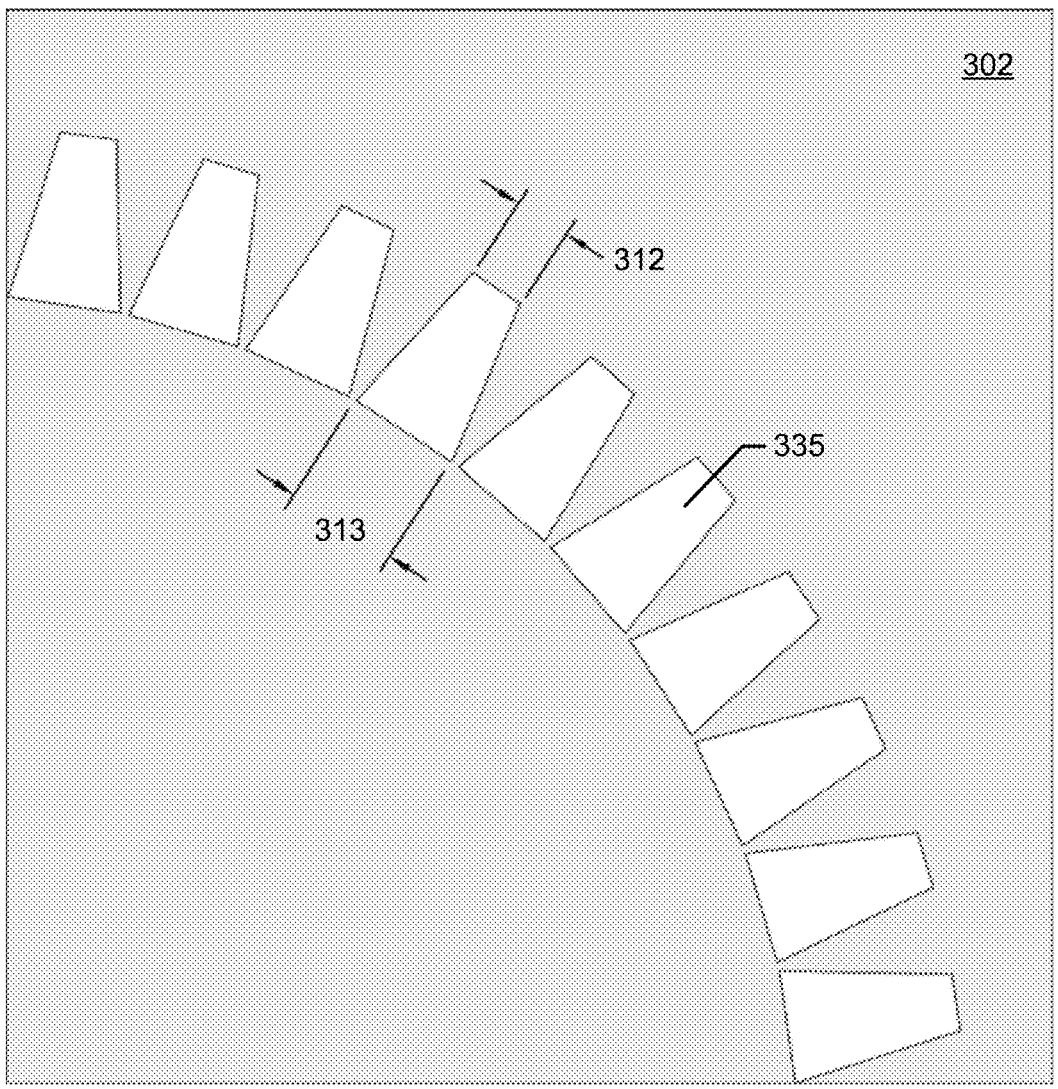

FIG. 3A is a top view schematic drawing of a ring resonator formed by a trapezoidal shaped pillar bend, in accordance with some embodiments. FIGS. 3B-3F are the cross-sections taken along the dashed lines D-D', E-E', F-F', G-G', and H-H' of FIG. 3A. FIG. 3G is a magnified schematic drawing showing a section of the trapezoidal shaped pillar of the ring resonator in FIG. 3A.

Figure 4A:
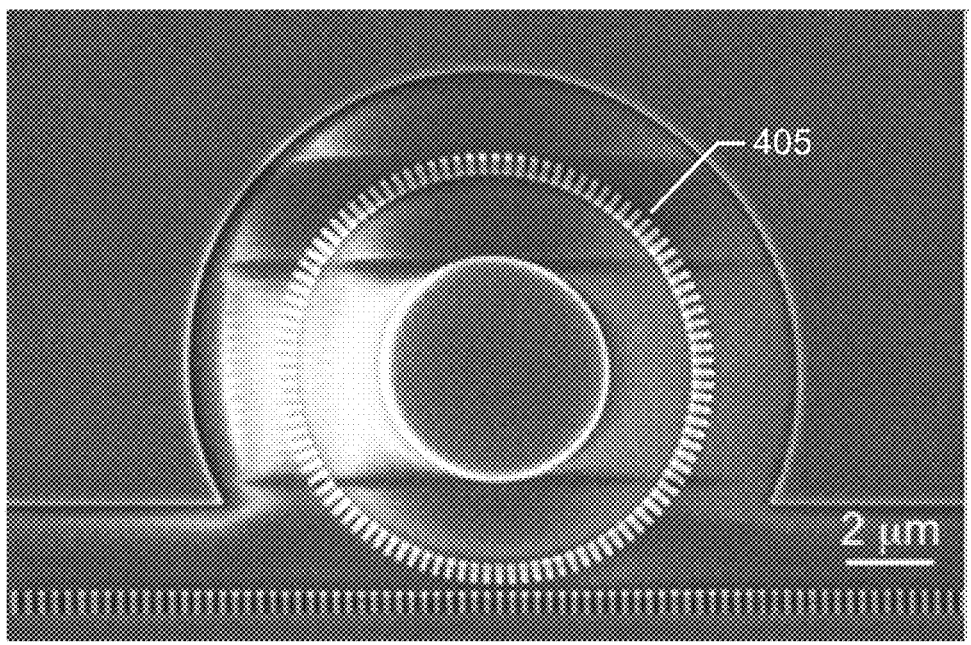
Figure 4B:
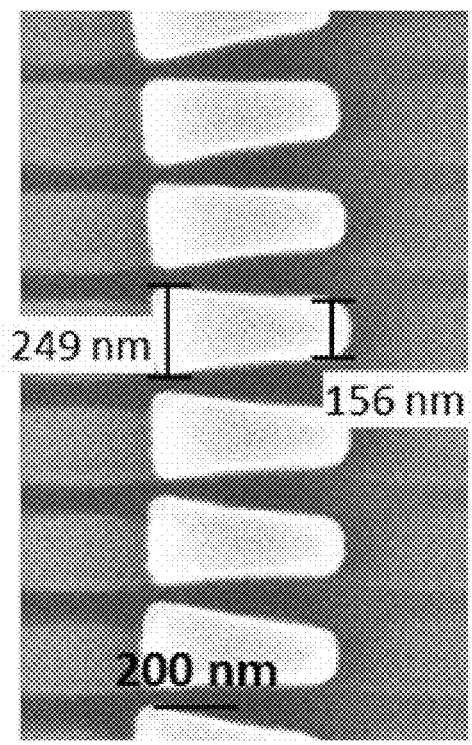
Figure 4C:
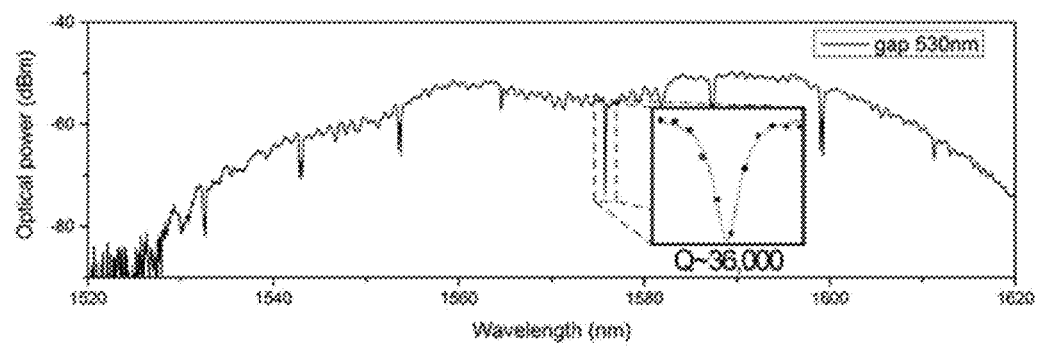
Figure 4D:
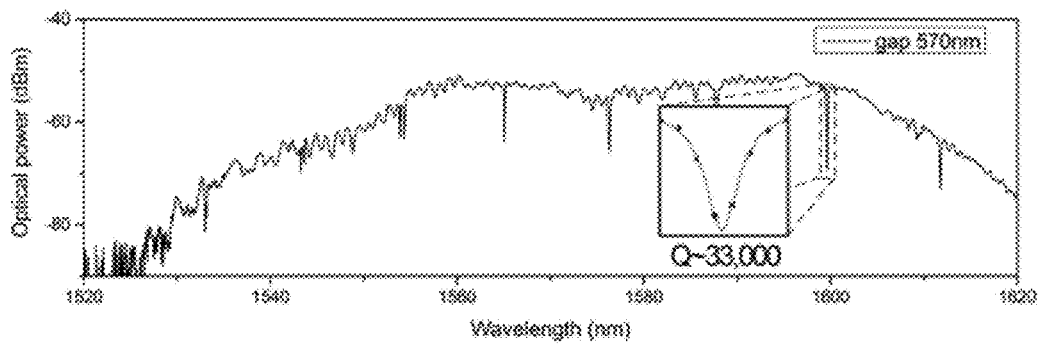
Figure 4E:
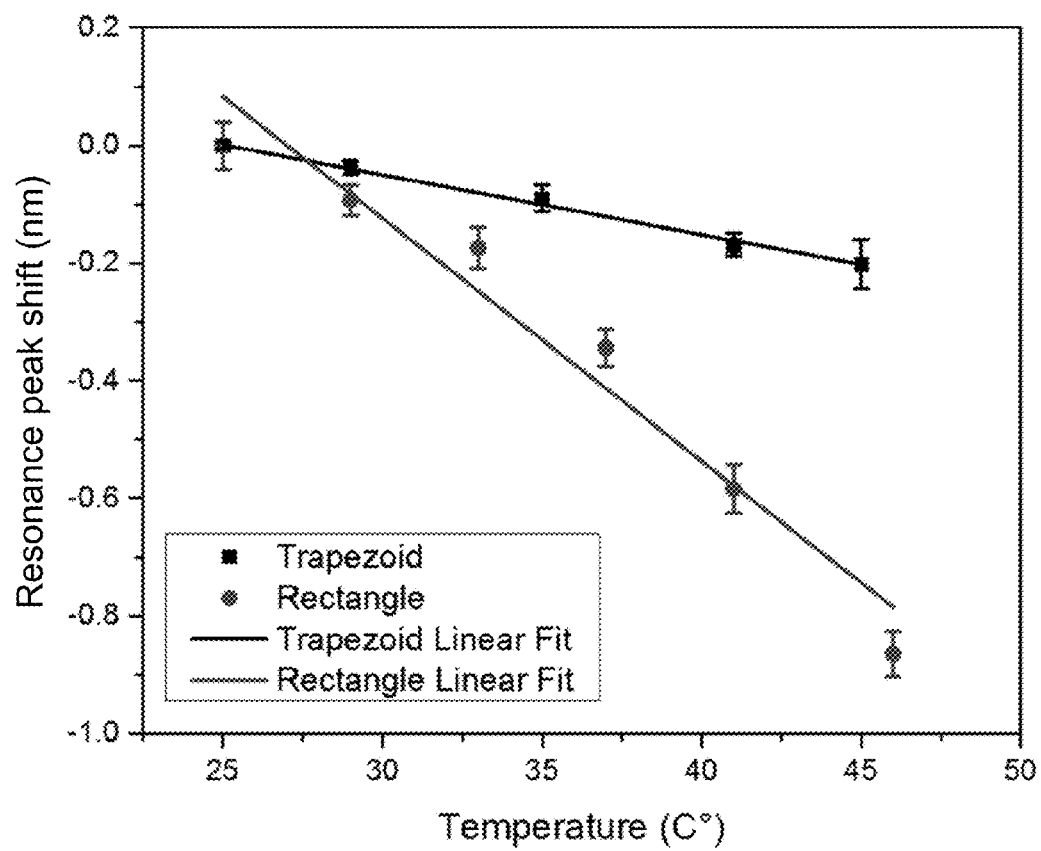

FIG. 4A is an SEM picture of a trapezoidal ring resonator, in accordance with some embodiments. FIG. 4B is a zoomed in picture showing the fabricated trapezoidal structures of FIG. 4A. FIG. 4C and FIG. 4D are the transmission spectra of ring resonators with gap sizes of 530 nm and 570 nm, respectively. FIG. 4E shows that with SU 8 cladding, the temperature sensitivity of the resonance may be reduced to 10 pm/° C.

Figure 5A:
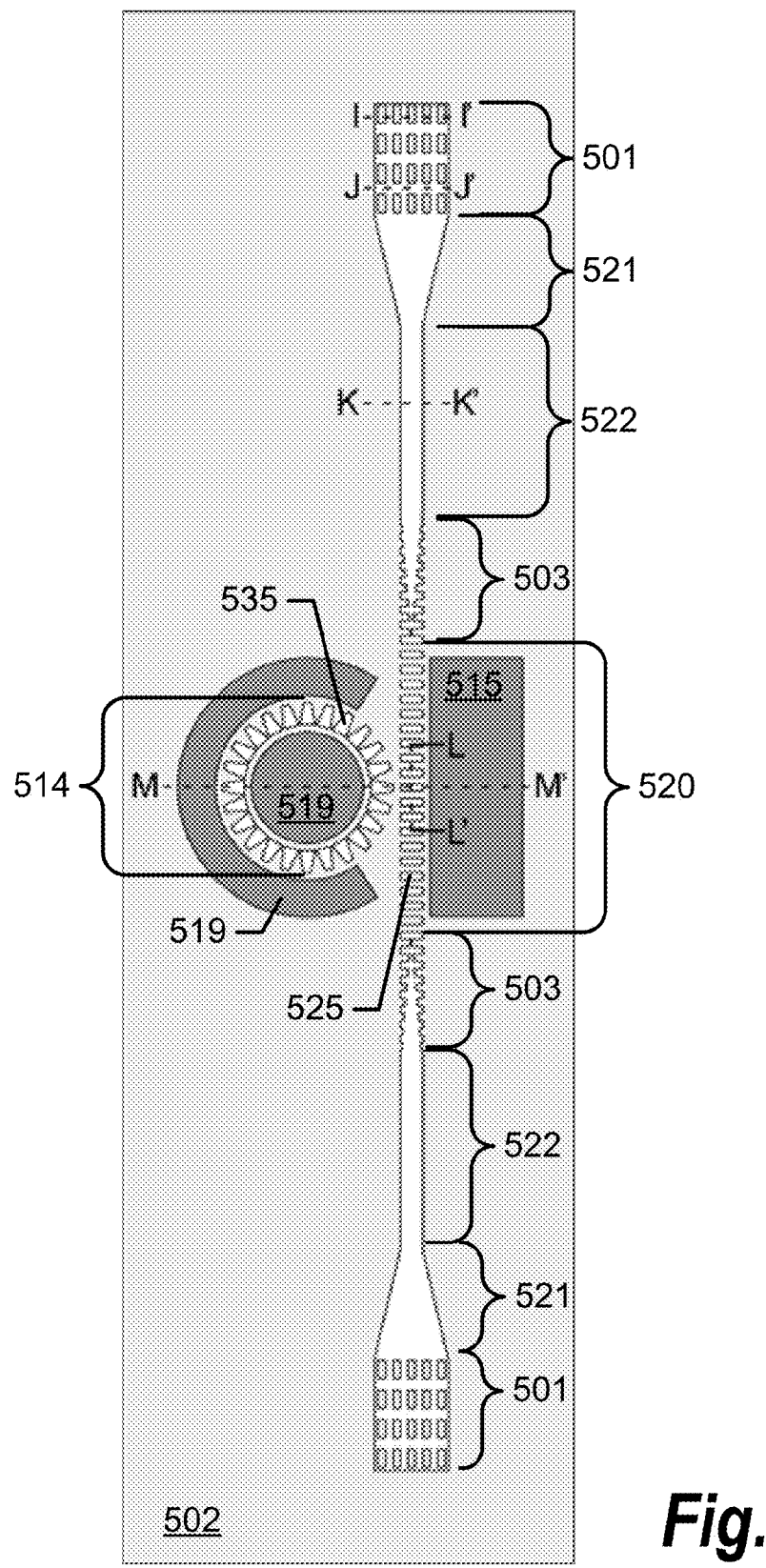
Figure 5D:
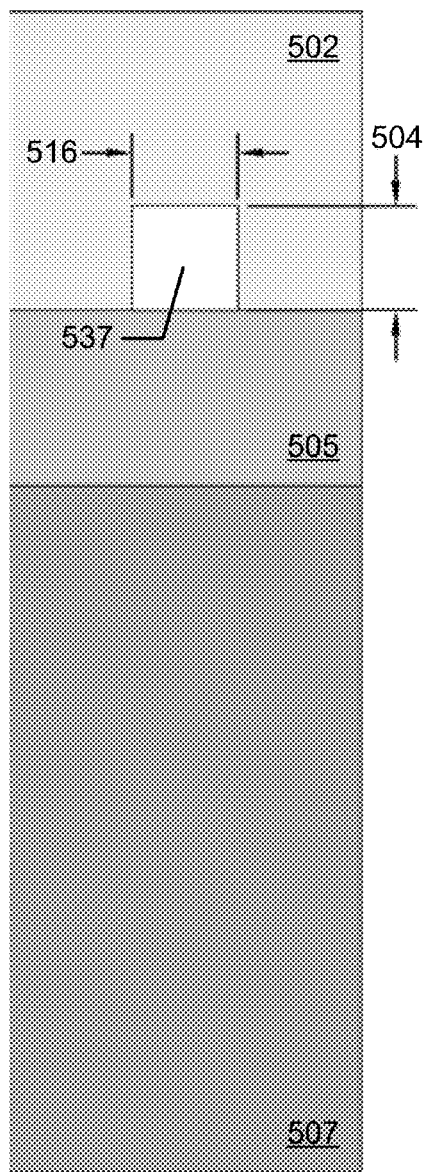
Figure 5E:
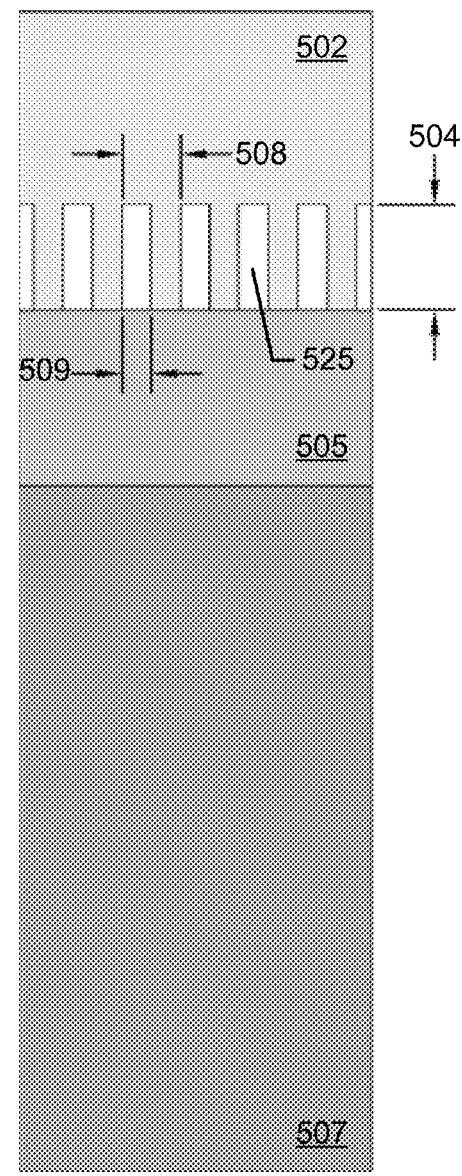
Figure 5F:
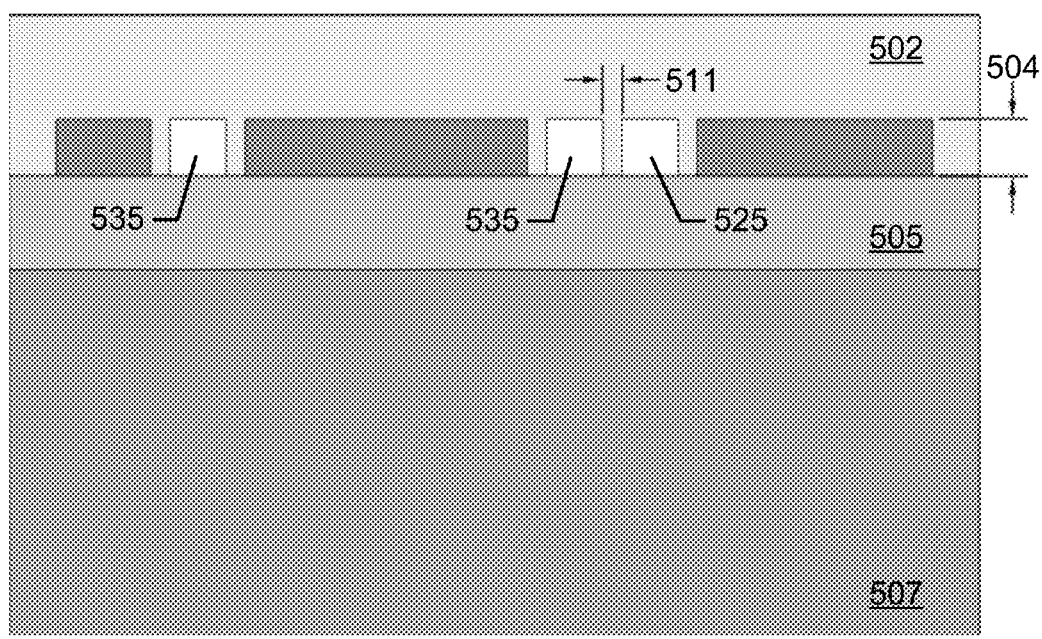
Figure 5G:
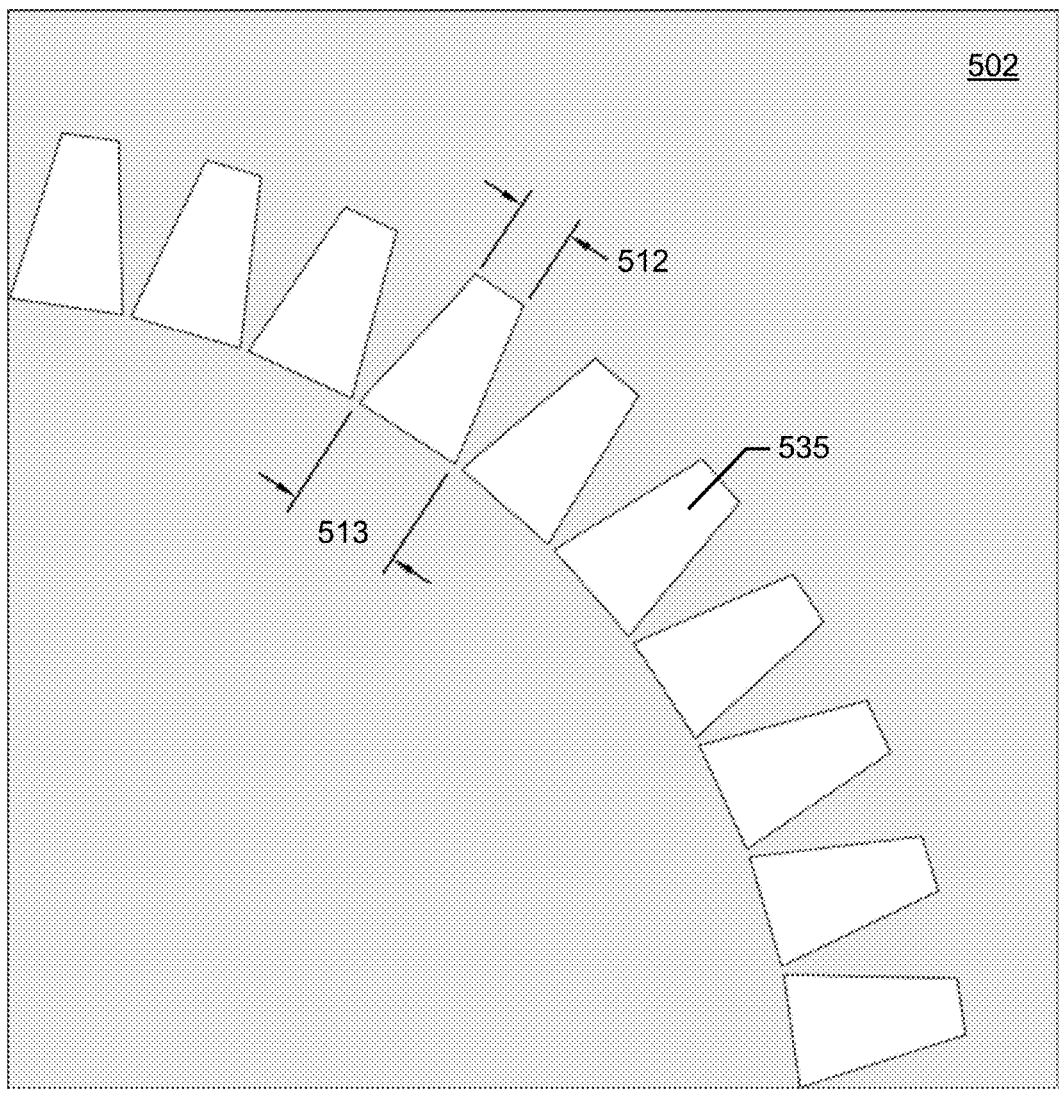

FIG. 5A is a top view schematic drawing of a modulator, in accordance with some embodiments. FIGS. 5B-5F are the cross-sections taken along the dashed lines I-I', J-J', K-K', L-L', and M-M' of FIG. 5A. FIG. 5G is a magnified schematic drawing showing a section of the trapezoidal shaped pillar of the ring resonator of the modulator in FIG. 5A.

Figure 6A:
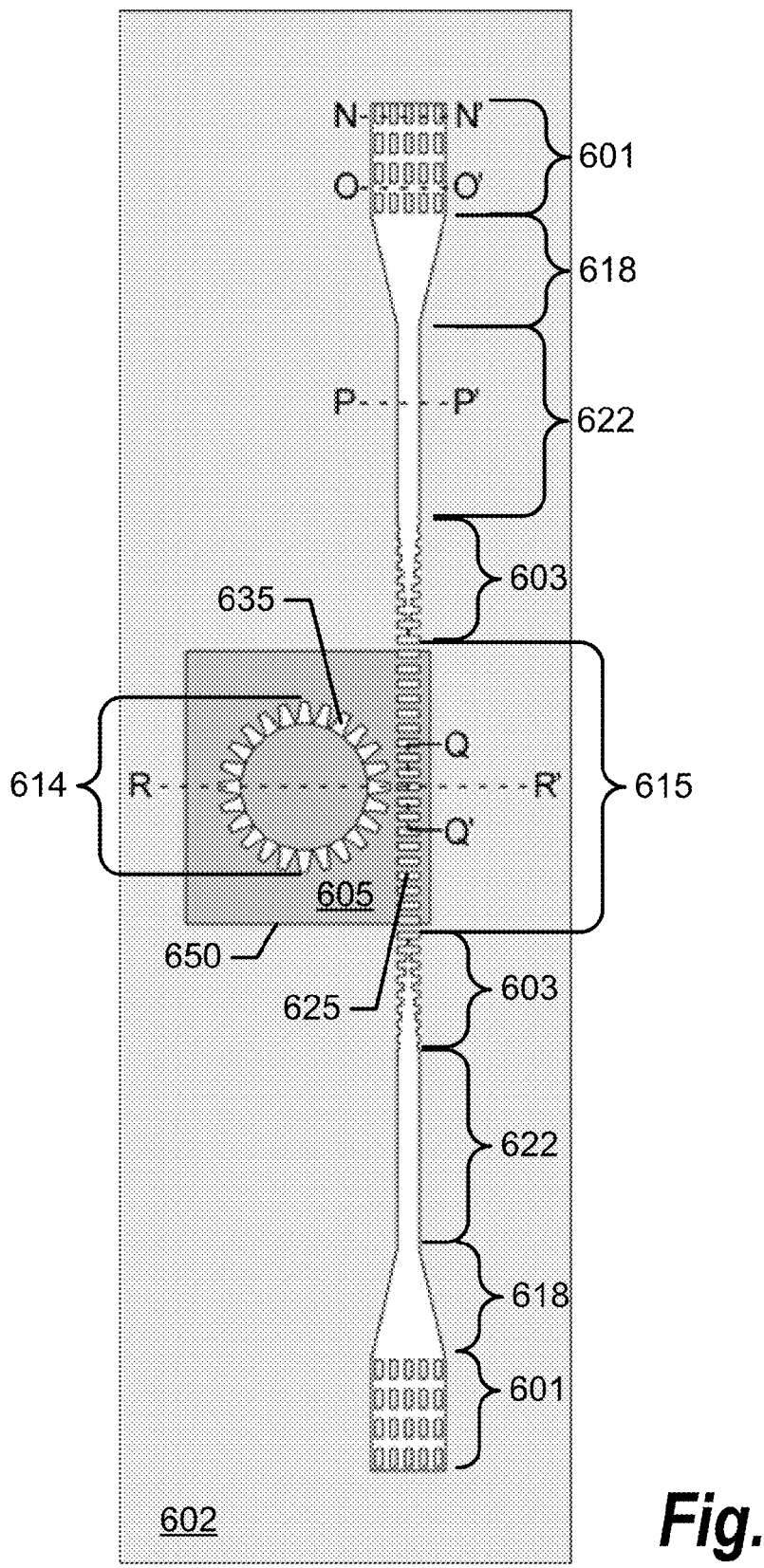
Figure 6F:
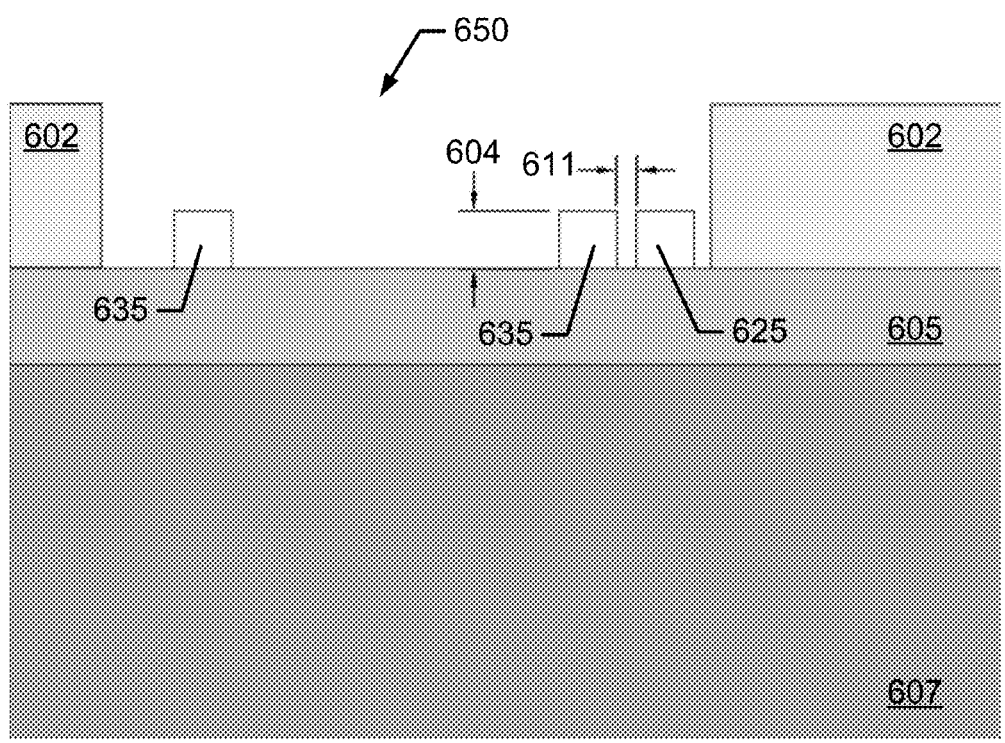
Figure 6G:
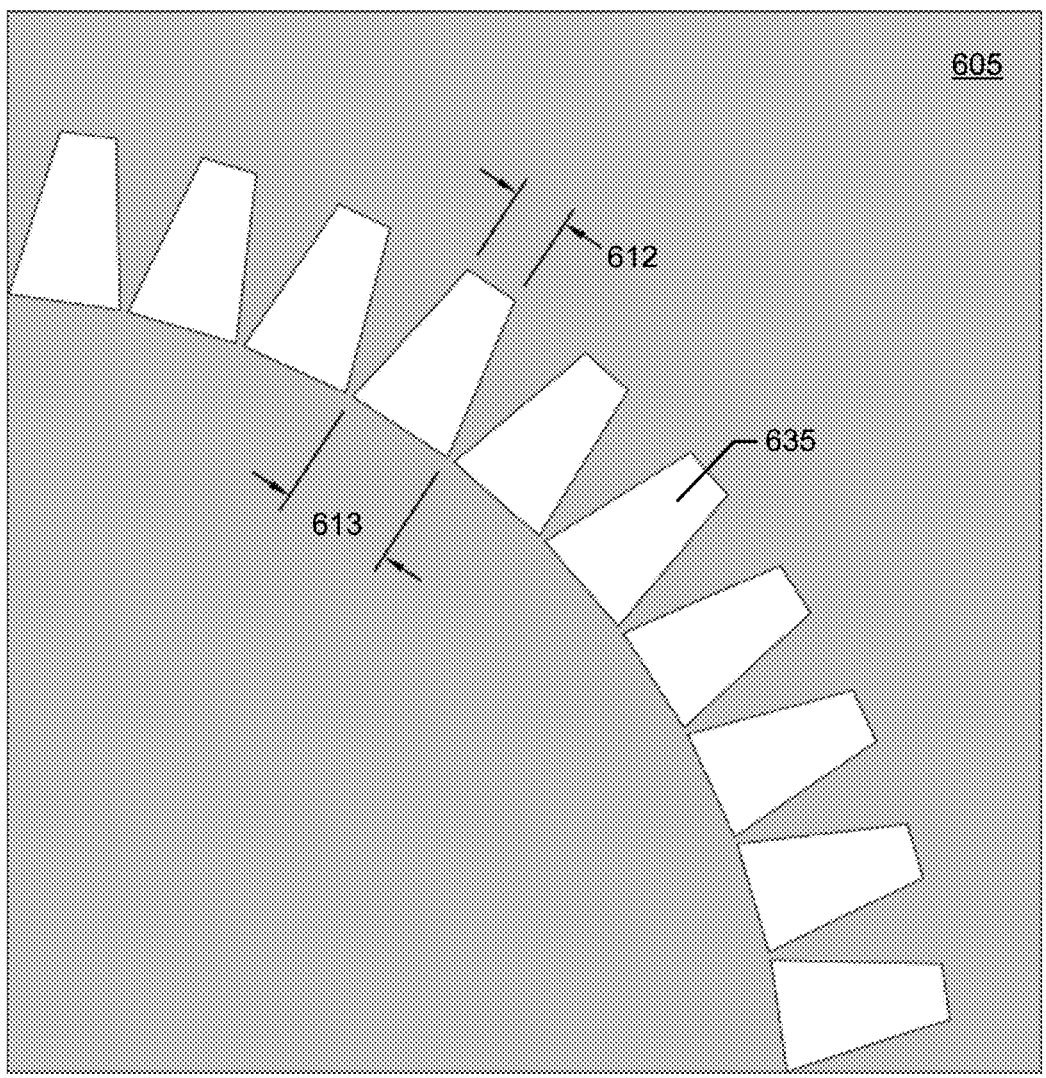

FIG. 6A is a top view schematic drawing of a sensor, in accordance with some embodiments. FIGS. 6B-6F are the cross-sections taken along the dashed lines N-N', O-O', P-P', Q-Q', and R-R' of FIG. 6A. FIG. 6G is a magnified schematic drawing showing a section of the trapezoidal shaped pillar of the ring resonator of the sensor in FIG. 6A.

Figure 7A:
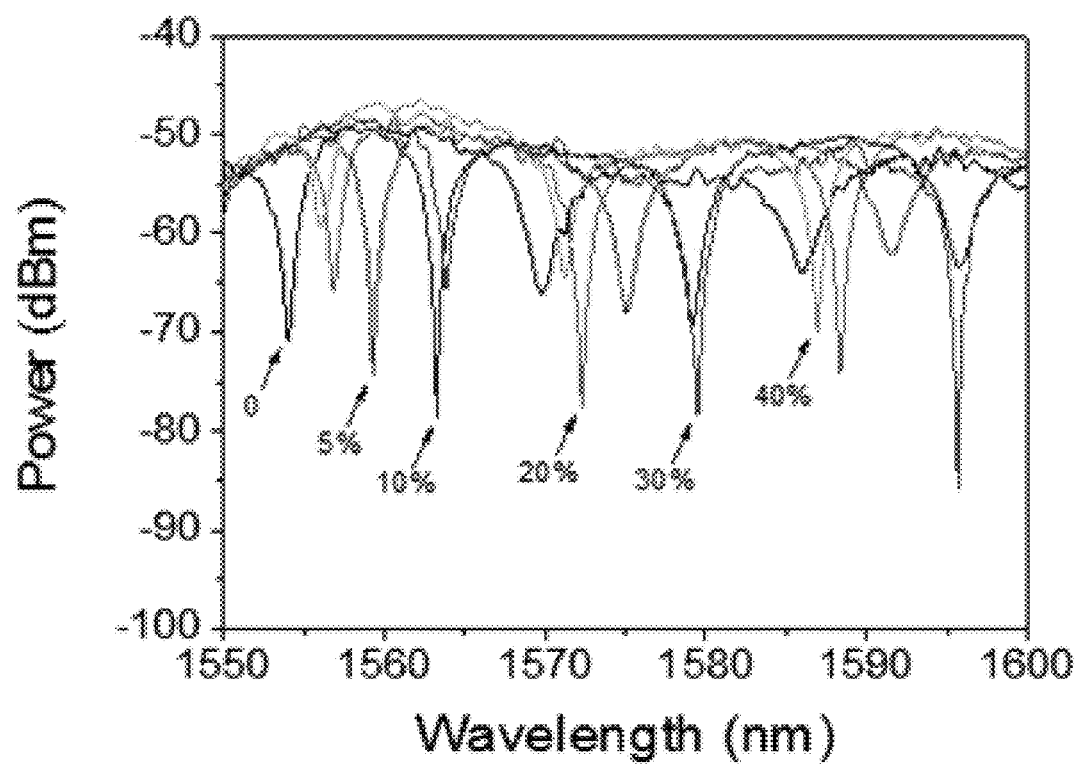
Figure 7B:
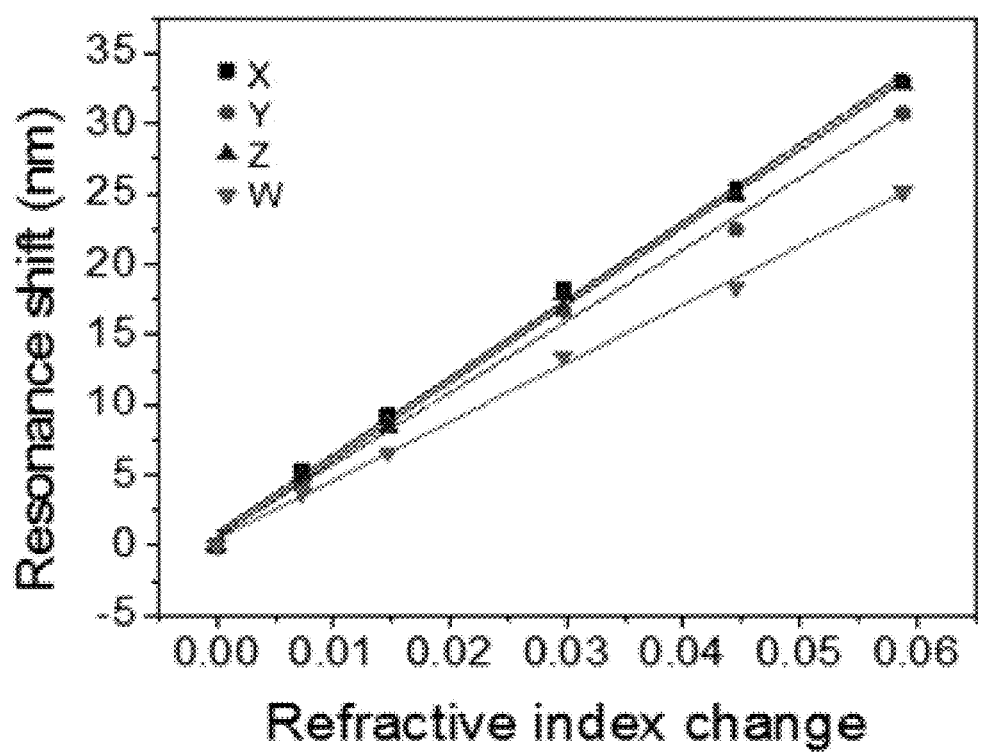

FIG. 7A is a graph showing the transmission spectra of the ring resonator when different concentrations of glycerol are applied. FIG. 7B is a graph showing the resonance shift versus ambient refractive index.

V. DETAILED DESCRIPTION

Detailed Description of the Invention

Detailed descriptions of the preferred embodiments are provided herein. It is to be understood, however, that the present invention may be embodied in various forms. The specific details disclosed herein are not to be interpreted as limiting, but rather as a basis for the claims and as representative basis for teaching one skilled in the art to employ the present invention in virtually any appropriately detailed system, structure, or manner. In all the accompanying drawings, same numerals are used within each figure to represent the same or similar materials, and redundant descriptions are omitted.

The invention discloses methods of reducing the loss of subwavelength photonic crystal waveguide bends and high quality factor subwavelength ring resonator based filters, modulators, and sensors. The low loss subwavelength photonic crystal waveguide bends are achieved by optimizing the shape of the dielectric pillars constituting the subwavelength photonic crystal waveguide to minimize the phase front distortion inside the bends. The disclosed trapezoidal shaped pillars may significantly reduce the bend loss. Subwavelength ring resonators based on the trapezoidal shaped pillars show a significantly improved quality factor and may be used to build devices such as a subwavelength photonic crystal bus waveguide, a subwavelength ring resonator with trapezoidal shaped dielectric pillars, input and output tapers to convert the strip waveguide mode into the subwavelength photonic crystal waveguide mode and vice versa, and couplers to couple light into and out from the chip. Light (from a broadband source or LED) coupled into the subwavelength photonic crystal waveguide couples with the resonance of the ring resonator and thereby drops the resonant wavelength into the resonator, leading to a minimum in the transmission spectrum of the ring resonator at the resonant wavelength. The resonance wavelength shifts in response to the change of ambient refractive index. Proper cladding materials are chosen to satisfy the requirement of different applications.

In FIG. 1A, a trapezoidal shaped subwavelength photonic crystal waveguide 103 is used to reduce the bend loss of the subwavelength photonic crystal waveguide 102. FIG. 1B, FIG. 1C, and FIG. 1D are the cross-sections taken along the dashed lines A-A', B-B', and C-C' of FIG. 1A, respectively. FIG. 1E is a magnified schematic drawing showing a section of the trapezoidal shaped pillar of the waveguide bend in FIG. 1A. The subwavelength photonic crystal waveguide is formed by periodically arranging the dielectric pillars 106. The optical properties, including dispersion, group velocity, mode volume overlap, etc., may be controlled by tuning the thickness 109, width 113, period 107, and depth 108 of the dielectric pillars 106. The subwavelength photonic crystal waveguide 102 and trapezoidal shaped subwavelength photonic crystal waveguide 103 are immersed in top cladding material 101 and rest upon bottom cladding 104. The substrate 105 may be a different material or the same material as bottom cladding 104. The propagation loss of a straight subwavelength photonic crystal waveguide is low due to the excitation of Bloch modes. However, the loss of a subwavelength photonic crystal waveguide bend is devastating. For instance, a 10 µm radius 90° bend has an insertion loss of ~1.5 dB. The bend loss may be significantly reduced by tuning the top width 111 and bottom width 110 of the series of trapezoidal shaped dielectric pillars 136 according to the bend radius 112. The bend radius has a center 120 from where the subwavelength photonic crystal waveguide bend is centered wherein the bottom width of the trapezoidal shaped dielectric pillars is closer to the center than the top width of the trapezoidal shaped dielectric pillars. The trapezoidal shaped dielectric pillars 136 have a trapezoid height 130 that is roughly equivalent to the width 113 of the subwavelength photonic crystal waveguide regions 102 that do not have a bend.

FIG. 2A is a scanning electron microscopy (SEM) image of a subwavelength photonic crystal waveguide bend comprising four 90° trapezoidal shaped dielectric pillar bends on a silicon-on-insulator platform, in accordance with some embodiments. To test the bending losses, four waveguide bend structure devices were manufactured as illustrated for one of the pillar designs in FIG. 2A. A waveguide bend structure device was made for each of the four types of silicon pillars: a non-tuned rectangular pillar (150 nm top base and 150 nm bottom base) pictured in FIG. 2B, a less-tuned trapezoidal pillar (120 nm top base and 190 nm bottom base) pictured in FIG. 2C, an over-tuned trapezoidal pillar (70 nm top base and 210 nm bottom base) pictured in FIG. 2E, and an optimally-tuned trapezoidal pillar (140 nm top base and 210 nm bottom base) pictured in FIG. 2D. The devices are made on an SOI (Silicon-On-Insulator) wafer manufactured by Soitec comprising a 250 nm thick top silicon layer (n=3.476) lying on a 3 µm thick buried oxide (BOX, n=1.45) layer. All structures are patterned in a single E-beam lithography step using a JEOL 6000 FSE. The patterns are then transferred into the underneath silicon layer through reactive-ion-etching using a PlasmaTherm 790. The agreement of the morphology of the devices with the design is confirmed by scanning electron microscopy (ZEISS Neon 40) as shown in FIGS. 2B-2E. Each device has four 90° bends. After spin-coating an SU-8 cladding, the devices are tested in a grating coupler alignment system. FIG. 2F shows the transmission spectra of the four subwavelength photonic crystal waveguide bends between 1540 nm and 1555 nm operating at the transverse electric (TE) mode. The insertion loss of the four representative bends at 1550 nm is shown graphically in FIG. 2G, where the optimized trapezoidal silicon pillars is as low as 1.37 dB per 90° bend, only 24.5% of that of the non-tuned rectangular silicon pillars (5.58 dB per 90° bend). When the pillars are over-tuned, the refractive index distortion and mode mismatch increases, and thus the loss increases. The experimental results demonstrate that the loss of subwavelength photonic crystal waveguide bends can be significantly reduced by optimizing the shapes of the silicon pillars.

FIG. 3A is a top view schematic drawing of a ring resonator all-optical switch based on the trapezoidal shaped subwavelength photonic crystal waveguide, wherein the ring resonator all-optical switch is immersed in top cladding material 302 and rests upon bottom cladding 305. FIGS. 3B, 3C, 3D, 3E, and 3F are the cross-sections taken along the dashed lines D-D', E-E', F-F', G-G', and H-H', respectively, of FIG. 3A and FIG. 3G is a magnified schematic drawing showing a section of the trapezoidal shaped pillars of the ring resonator in FIG. 3A. The ring resonator is formed by a circular ring of trapezoidal shaped high refractive index dielectric pillars 335 of sufficient height 304 sitting on top of the bottom cladding 305, as illustrated in FIGS. 3A, 3F, and 3G. The whole structure is supported by a substrate 307. The ring resonator 314 is side-coupled to a bus waveguide 315 which is a conventional subwavelength photonic crystal waveguide, with dielectric pillars 325 of period 308, depth 309, and height 304, as illustrated in FIG. 3E. The coupling strength between the bus waveguide and the ring resonator is tuned by the gap 311, as illustrated in FIG. 3F. To achieve a high quality factor, the top width 312 and bottom width 313 of the trapezoidal shaped dielectric pillars 335 are tuned to minimize the loss, as illustrated in FIG. 3G. The coupling strength is adjusted accordingly to meet the coupling requirements and achieve a high quality factor. To facilitate a lossless transition between strip waveguide 316 and subwavelength photonic crystal waveguide 315, an inverse taper 303 with fins of increasing length is adopted. The number of periods, the position, and the length of the fins may be tuned to further enhance the transmission at wavelengths of interest. Subwavelength grating couplers 301 are designed to couple light from optical fibers into the on-chip circuit. The coupling efficiency of the grating coupler may be optimized by tuning the subwavelength grating period 306 and filling factor 317 of the dielectric pillars 347 with a height 304, as illustrated in FIG. 3B. The subwavelength grating couplers 301 have a height 304 and width 310, as illustrated in FIG. 3C. An adiabatic taper 318 is used to bridge the grating coupler regions 301 and the strip waveguides 316. The subwavelength grating coupler has a width 310 around 10 µm and the single mode waveguide 337 has a width 336 around 500 nm and a height 304, as illustrated in FIG. 3C and FIG. 3D, respectively. For all-optical switches, materials 302 with large third-order nonlinearity and small third-order absorption are applied through spin-casting, deposition, or transferring. These materials include but are not limited to 2D materials (graphene, graphene oxide, etc.), polymer (DDMBT, etc.), and semiconductor materials (silicon nitride, etc.). A pump is either coupled into the waveguide together with the probe through grating couplers 301 or incidents vertically onto the ring resonator without coupling into the waveguide. The pump may be generated by a modulated continuous-working laser or a pulsed laser. The wavelength of the probe is fixed at one resonance frequency of the ring resonator. When the pump is off, the output of the probe reaches the minimum and the switch is turned off. When the pump is on, the refractive index change of the cladding material shifts the resonance of the resonator. As a result, the output of the probe light increases and the switch is turned on.

The same structure illustrated in FIGS. 3A-3G may also be used for athermal devices when the thermo-optic coefficients of the cladding 302 and the subwavelength dielectric pillars 325, 335 have opposite signs. The equivalent thermo-coefficient of the structure equals zero when the period 308 and the depth 309 of the dielectric pillars 325 and the top width 312 and bottom width 313 of the trapezoidal shaped dielectric pillars 335 are designed properly.

FIG. 4A is an SEM image of a fabricated subwavelength ring resonator 405 with a 10 µm bending radius. FIG. 4B is a magnified SEM image showing the shape of the trapezoidal shaped dielectric pillars. The top width of the trapezoidal shaped dielectric pillars of the subwavelength ring resonator is 156 nm and the bottom width is 249 nm. FIG. 4C and FIG. 4D are the transmission spectra of the trapezoidal ring resonators with gap sizes of 530 nm and 570 nm, respectively. The transmission spectra are obtained by coupling a broadband light source into the device through the coupler on one end, and analyzing the light coupled out from the other end with an optical spectrum analyzer. The quality factor of the subwavelength ring resonator may be tuned by the gap size between the bus waveguide and the ring resonator. The quality factor is defined as the ratio of the energy stored in the oscillating resonator to the energy dissipation rate and can be calculated by taking the ratio of the resonance wavelength, $\lambda_{res}$, to the full width at half maximum, $\Delta\lambda$. When the gap size is 530 nm, the quality factor is about 36,000, as shown and magnified in the inset box in FIG. 4C and when the gap size increases to 570 nm, the quality factor reduces to about 33,000 as shown and magnified in the inset box in FIG. 4D. FIG. 4E shows that combining two materials of positive and negative thermo-optic coefficients can cancel the temperature dependence of the ring resonator device. The results show that the temperature sensitivity may be reduced to −10 pm/° C., thus making temperature independent devices possible with the optimization of the size of the trapezoidal shaped dielectric pillars.

FIG. 5A is a top view schematic drawing of a hybrid optical modulator based on a subwavelength ring resonator, wherein the hybrid optical modulator is immersed in top cladding material 502 and rests upon bottom cladding 505. FIGS. 5B, 5C, 5D, 5E, and 5F are the cross-sections taken along the dashed lines I-I', K-K', L-L', and M-M', respectively, of FIG. 5A and FIG. 5G is a magnified schematic drawing showing a section of the trapezoidal shaped pillars of the ring resonator of the modulator in FIG. 5A. The ring resonator is formed by a circular ring of trapezoidal shaped high refractive index dielectric pillars 535 of sufficient height 504 sitting on top of the bottom cladding 505, as illustrated in FIGS. 5A, 5F, and 5G. The whole structure is supported by a substrate 507. The ring resonator 514 is side-coupled to a bus waveguide 520 which is a conventional subwavelength photonic crystal waveguide, with dielectric pillars 525 of period 508, depth 509, and height 504, as illustrated in FIG. 5E. The coupling strength between the bus waveguide and the ring resonator is tuned by the gap 511, as illustrated in FIG. 5F. To achieve a high quality factor, the top width 512 and bottom width 513 of the trapezoidal shaped dielectric pillars 535 are tuned to minimize the loss, as illustrated in FIG. 5G. The coupling strength is adjusted accordingly to meet the coupling requirements and achieve a high quality factor. To facilitate a lossless transition between strip waveguide 522 and subwavelength photonic crystal waveguide 520, an inverse taper 503 with fins of increasing length is adopted. The number of periods, the position, and the length of the fins may be tuned to further enhance the transmission at wavelengths of interest. Subwavelength grating couplers 501 are designed to couple light from optical fibers into the on-chip circuit. The coupling efficiency of the grating coupler may be optimized by tuning the subwavelength grating period 506 and filling factor 517 of the dielectric pillars 547 with a height 504, as illustrated in FIG. 5B. The subwavelength grating couplers 501 have a height 504 and width 510, as illustrated in FIG. 5C. An adiabatic taper 521 is used to bridge the grating coupler regions 501 and the strip waveguides 522. The subwavelength grating coupler has a width 510 around 10 μm and the single mode waveguide 537 has a width 516 around 500 nm and a height 504, as illustrated in FIG. 5C and FIG. 5D, respectively. Materials with high electro-optic coefficient are used as the cladding material 502. These materials include polymers, 2D materials, etc. An electrical signal may be added upon the modulator through two electrodes 519. The electrodes may be put in-plane with the waveguide or on-top of the cladding material. If the electrodes are in-plane, then one electrode will be atop the bottom cladding and within the circular ring of trapezoidal shaped dielectric pillars and another electrode will be atop the bottom cladding and substantially surrounding the circular ring of trapezoidal shaped dielectric pillars. If the electrodes are on-top of the cladding material, one electrode will be within a surface normal projection of the circular ring of trapezoidal shaped dielectric pillars and a second electrode will be substantially surrounding the surface normal projection of the circular ring of trapezoidal shaped dielectric pillars. Essentially as shown in FIG. 5A the electrodes 519 would be positioned the same relative to the ring resonator but would be atop the top cladding instead of the bottom cladding. The modulation is achieved by aligning a single wavelength laser to a resonance wavelength of the resonator 514 and modulating the resonant wavelength using the two metal electrodes 519. The refractive index of the cladding material changes with the external fields and therefore the resonance wavelength shifts. As a result, the output optical intensity changes with the external electrical field. To compensate fabrication error induced resonance shift and environmental temperature variation, an additional electrode 515 may be placed adjacent to the bus waveguide 520 as a heater. The coupling coefficient of the bus waveguide 520 and ring resonator 514 may be adjusted by tuning the temperature through the electrode 515. The ring resonator may also be used as an electromagnetic wave sensor when the electrodes 519 are replaced by antennas.

FIG. 6A is a top view schematic drawing of an ultrasensitive sensor which may be used for chemical detection, spectroscopy, and biosensing, wherein most of the ultrasensitive sensor is immersed in top cladding material 602 with the exception of a window 650 where a chemical or other biomolecule may interact with the ring resonator 614 and bus waveguide 615 of the ultrasensitive sensor. The ultrasensitive sensor rests upon bottom cladding 605. FIGS. 6B, 6C, 6D, 6E, and 6F are the cross-sections taken along the dashed lines N-N', O-O', P-P', Q-Q', and R-R', respectively, of FIG. 6A and FIG. 6G is a magnified schematic drawing showing a section of the trapezoidal shaped pillars of the ring resonator of the ultrasensitive sensor in FIG. 6A. The ring resonator is formed by a circular ring of trapezoidal shaped high refractive index dielectric pillars 635 of sufficient height 604 sitting on top of the bottom cladding 605, as illustrated in FIGS. 6A, 6F, and 6G. The whole structure is supported by a substrate 607. The ring resonator 614 is side-coupled to a bus waveguide 615 which is a conventional subwavelength photonic crystal waveguide, with dielectric pillars 625 of period 608 and depth 609, as illustrated in FIG. 6E. The coupling strength between the bus waveguide and the ring resonator is tuned by the gap 611, as illustrated in FIG. 6F. To achieve a high quality factor, the top width 612 and bottom width 613 of the dielectric pillars are tuned to minimize the loss, as illustrated in FIG. 6G. The coupling strength is adjusted accordingly to meet the coupling requirement and achieve a high quality factor. To facilitate a lossless transition between strip waveguide 622 and subwavelength photonic crystal waveguide 615, an inverse taper 603 with fins of increasing length is adopted. The number of periods, the position, and the length of the fins may be tuned to further enhance the transmission at wavelengths of interest. Subwavelength grating couplers 601 are designed to couple light from optical fibers into the on-chip circuit. The coupling efficiency of the grating coupler may be optimized by tuning the subwavelength grating period 606 and filling factor 617 of the dielectric pillars 647, as illustrated in FIG. 6B. The subwavelength grating couplers 601 have a height 604 and width 610, as illustrated in FIG. 6C. An adiabatic taper 618 is used to bridge the grating coupler regions 601 and the strip waveguides 622. The subwavelength grating coupler has a width 610 around 10 μm and the single mode waveguide 637 has a width 616 around 500 nm and a height 604 around 250 nm, as illustrated in FIG. 6C and FIG. 6D, respectively. The resonance wavelength of the ring resonator shifts in response to the change of the ambient refractive index due to a substance coming in contact with the ring resonator 614 through the window 650. The ultrasensitive sensor may be used to detect organic or inorganic substances such as proteins, DNA, RNA, small molecules, nucleic acids, virus, bacteria, cells, genes, without the use of labels such as fluorescence or radiometry.

As a demonstration of the reduced loss and improved quality factor of the disclosed subwavelength grating ring resonator. Four devices that comprise ring resonators with 10 μm radius based on trapezoidal shaped dielectric pillars and subwavelength photonic crystal waveguides were characterized with different concentrations of glycerol solution. Three of the devices comprise regular rectangular shaped subwavelength photonic crystal waveguides in the ring resonator and one of the devices comprises trapezoidal shaped dielectric pillar based subwavelength photonic crystal waveguides in the ring resonator. All the subwavelength photonic crystal waveguides have a width of 500 nm, a period of 300 nm, a thickness of 250 nm, and a depth of 150 nm. The top and bottom width of the trapezoidal pillars are 140 nm and 210 nm, respectively. The devices are made on an SOI wafer manufactured by Soitec comprising a 250 nm thick top silicon layer (n=3.476) lying on a 3 μm thick buried oxide (BOX, n=1.45) layer. All structures are patterned in a single E-beam lithography step using a JEOL 6000 FSE. The patterns are then transferred into the underneath silicon layer through reactive-ion-etching using a PlasmaTherm 790. Samples with different refractive index were prepared from different concentrations of glycerol-water solutions. Table I lists the refractive indices of glycerol-water solution with glycerol percentage by volume ranging from 0 to 25 percent.

TABLE I

Absorption peak wavelength of gas molecules.

| Glycerol % by volume | Refractive index |
|---|---|
| 0 | 1.33303 |
| 5 | 1.33880 |
| 10 | 1.34481 |
| 15 | 1.35106 |
| 20 | 1.35749 |
| 25 | 1.36404 |

Solutions with different glycerol concentrations were applied on the top of the four ring resonator devices one at a time and the optical spectra were obtained from an optical spectrum analyzer each time. FIG. 7A shows the transmission spectra of one of the four devices from 1550 nm to 1600 nm with different glycerol concentration solutions. The resonance peaks shift to longer wavelength with increasing glycerol concentration (increasing refractive index). Based on the resonance shift obtained from the optical spectra and the corresponding refractive index data listed in Table I, the resonance wavelength shift versus change in refractive index figure is shown in the graph of FIG. 7B. The datasets for X, Y, and Z are for three of the devices with regular rectangular shaped subwavelength photonic crystal waveguides in the ring resonator and the dataset for W is for the device with trapezoidal shaped dielectric pillar based subwavelength photonic crystal waveguides in the ring resonator. Applying a linear fit to the datasets reveals a bulk refractive index sensitivity of approximately 510~550 nm/refractive index unit (RIU) for the devices with regular shaped subwavelength photonic crystal waveguides in the ring resonator and approximately 420 nm/RIU for the device with trapezoidal shaped dielectric pillar based subwavelength photonic crystal waveguides in the ring resonator. Thus disclosing that the trapezoidal shaped dielectric pillar based ring resonator may be used as a fundamental building block for ultrafast and low power consumption all-optical switches, athermal resonators, modulators, and ultrasensitive sensors.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions, and improvements to the embodiments described above are possible. It is contemplated that these variations, modifications, additions and improvements fall within the scope of the invention as detailed within the following claims.

The invention claimed is:

1. A method for reducing loss in a subwavelength photonic crystal waveguide bend comprising:
    forming the subwavelength photonic crystal waveguide bend with a series of trapezoidal shaped dielectric pillars centered about a bend radius;
    wherein each of the trapezoidal shaped dielectric pillars comprise a top width, a bottom width, and a trapezoid height;
    wherein the length of the bottom width is greater than the length of the top width; and wherein the bottom width is closer to the center of the bend radius of the subwavelength photonic crystal waveguide bend than the top width.

2. An optical system comprising:
a substrate;
a bottom cladding disposed on the substrate;
a subwavelength photonic crystal waveguide atop the bottom cladding; and
a ring resonator atop the bottom cladding and side-coupled by a gap to the subwavelength photonic crystal waveguide;
wherein the ring resonator comprises a circular ring of trapezoidal shaped dielectric pillars;
wherein each of the trapezoidal shaped dielectric pillars comprise a top width, a bottom width, and a trapezoid height;
wherein the length of the bottom width is greater than the length of the top width; and
wherein the bottom width is closer to the center of the circular ring of trapezoidal shaped dielectric pillars than the top width.

3. The optical system of claim 2, further comprising:
an input inverse taper atop the bottom cladding and coupled to the subwavelength photonic crystal waveguide;
an input strip waveguide atop the bottom cladding and coupled to the input inverse taper opposite the subwavelength photonic crystal waveguide;
an input adiabatic taper atop the bottom cladding and coupled to the input strip waveguide opposite the input inverse taper; and
an input subwavelength grating coupler atop the bottom cladding and coupled to the input adiabatic taper opposite the input strip waveguide.

4. The optical system of claim 3, further comprising:
a top cladding atop the bottom cladding, the subwavelength photonic crystal waveguide, the ring resonator, the input inverse taper, the input strip waveguide, the input adiabatic taper, and the input subwavelength grating coupler.

5. The optical system of claim 4, wherein the top cladding comprises a second-order nonlinear material or a third-order nonlinear material.

6. The optical system of claim 4, wherein the thermo-optical coefficient of the top cladding and the dielectric pillars of the subwavelength photonic crystal waveguide and the ring resonator are oppositely signed.

7. The optical system of claim 3, further comprising:
a top cladding atop the bottom cladding, the input inverse taper, the input strip waveguide, the input adiabatic taper, and the input subwavelength grating coupler; and
a window over the subwavelength photonic crystal waveguide and the ring resonator, wherein the window is void of the top cladding and is configured to expose the subwavelength photonic crystal waveguide and the ring resonator.

8. The optical system of claim 3, further comprising:
an output inverse taper atop the bottom cladding and coupled to the subwavelength photonic crystal waveguide opposite the input inverse taper;
an output strip waveguide atop the bottom cladding and coupled to the output inverse taper opposite the subwavelength photonic crystal waveguide;
an output adiabatic taper atop the bottom cladding and coupled to the output strip waveguide opposite the output inverse taper; and
an output subwavelength grating coupler atop the bottom cladding and coupled to the output adiabatic taper opposite the output strip waveguide.

9. The optical system of claim 8, further comprising:
a top cladding atop the bottom cladding, the subwavelength photonic crystal waveguide, the ring resonator, the input inverse taper, the input strip waveguide, the input adiabatic taper, the input subwavelength grating coupler, the output inverse taper, the output strip waveguide, the output adiabatic taper, and the output subwavelength grating coupler.

10. The optical system of claim 9, wherein the top cladding comprises a second-order nonlinear material or a third-order nonlinear material.

11. The optical system of claim 9, wherein the thermo-optical coefficient of the top cladding and the dielectric pillars of the subwavelength photonic crystal waveguide and the ring resonator are oppositely signed.

12. The optical system of claim 8, further comprising:
a top cladding atop the bottom cladding, the input inverse taper, the input strip waveguide, the input adiabatic taper, the input subwavelength grating coupler, the output inverse taper, the output strip waveguide, the output adiabatic taper, and the output subwavelength grating coupler; and
a window over the subwavelength photonic crystal waveguide and the ring resonator, wherein the window is void of the top cladding and is configured to expose the subwavelength photonic crystal waveguide and the ring resonator.

13. The optical system of claim 2, further comprising:
a first electrode atop the bottom cladding and within the circular ring of trapezoidal shaped dielectric pillars; and
a second electrode atop the bottom cladding and substantially surrounding the circular ring of trapezoidal shaped dielectric pillars.

14. The optical system of claim 2, further comprising:
a heater electrode atop the bottom cladding and adjacent the subwavelength photonic crystal waveguide opposite the ring resonator.

15. The optical system of claim 2, further comprising:
a top cladding atop the bottom cladding, the subwavelength photonic crystal waveguide, and the ring resonator.

16. The optical system of claim 15, further comprising:
a first electrode atop the top cladding and within a surface normal projection of the circular ring of trapezoidal shaped dielectric pillars; and
a second electrode atop the top cladding and substantially surrounding the surface normal projection of the circular ring of trapezoidal shaped dielectric pillars.

17. An optical system comprising:
a substrate;
a bottom cladding disposed on the substrate; and
a subwavelength photonic crystal waveguide bend atop the bottom cladding;
wherein the subwavelength photonic crystal waveguide bend comprises a series of trapezoidal shaped dielectric pillars centered about a bend radius;
wherein each of the trapezoidal shaped dielectric pillars comprise a top width, a bottom width, and a trapezoid height;
wherein the length of the bottom width is greater than the length of the top width; and wherein the bottom width is closer to the center of the bend radius of the subwavelength photonic crystal waveguide bend than the top width.

\* \* \* \* \*